(12) United States Patent
Herr et al.

(10) Patent No.: US 9,872,782 B2
(45) Date of Patent: Jan. 23, 2018

(54) BIOMIMETIC JOINT ACTUATORS

(71) Applicant: BionX Medical Technologies, Inc., Bedford, MA (US)

(72) Inventors: Hugh Miller Herr, Somerville, MA (US); Jeff Anthony Weber, San Francisco, CA (US); Richard James Casler, Lowell, MA (US)

(73) Assignee: BIONX MEDICAL TECHNOLOGIES, INC., Bedford, MA (US)

( * ) Notice: Subject to any disclaimer, the term of this patent is extended or adjusted under 35 U.S.C. 154(b) by 0 days.

(21) Appl. No.: 14/734,662

(22) Filed: Jun. 9, 2015

(65) Prior Publication Data

US 2015/0265427 A1  Sep. 24, 2015

Related U.S. Application Data

(62) Division of application No. 13/417,949, filed on Mar. 12, 2012, now Pat. No. 9,060,883.

(Continued)

(51) Int. Cl.
*A61F 2/66* (2006.01)
*A61F 2/68* (2006.01)
(Continued)

(52) U.S. Cl.
CPC ............... *A61F 2/68* (2013.01); *A61F 2/605* (2013.01); *A61F 2/64* (2013.01); *A61F 2/66* (2013.01);
(Continued)

(58) Field of Classification Search
CPC ........ A61F 2002/6607; A61F 2002/741; A61F 2002/6818; B25J 9/0006
See application file for complete search history.

(56) References Cited

U.S. PATENT DOCUMENTS 2,489,291 A  11/1949 Henschke et al.
2,529,968 A  11/1950 Sartin
(Continued)

FOREIGN PATENT DOCUMENTS

EP   1393866        3/2004
WO   WO-2003068453  8/2003
(Continued)

OTHER PUBLICATIONS

Martinez-Villalpando. Agonist-antagonist active knee prosthesis: A preliminary study in level-ground walking. Journal of Rehabilitation Research & Development. vol. 46, No. 3, 2009. pp. 361-374.*
(Continued)

*Primary Examiner* — Thomas J Sweet
*Assistant Examiner* — Christie Bahena

(57) ABSTRACT

In a powered actuator for supplying torque, joint equilibrium, and/or impedance to a joint, a motor is directly coupled to a low-reduction ratio transmission, e.g., a transmission having a gear ratio less than about 80 to 1. The motor has a low dissipation constant, e.g., less than about 50 $W/(Nm)^2$. The transmission is serially connected to an elastic element that is also coupled to the joint, thereby supplying torque, joint equilibrium, and/or impedance to the joint while minimizing the power consumption and/or acoustic noise of the actuator.

6 Claims, 6 Drawing Sheets

Related U.S. Application Data

(60) Provisional application No. 61/451,887, filed on Mar. 11, 2011.

(51) Int. Cl.
*A61F 2/70* (2006.01)
*A61F 2/76* (2006.01)
*A61F 2/60* (2006.01)
*A61F 2/64* (2006.01)

(52) U.S. Cl.
CPC .... *A61F 2/6607* (2013.01); *A61F 2002/6664* (2013.01); *A61F 2002/6809* (2013.01); *A61F 2002/6836* (2013.01); *A61F 2002/701* (2013.01); *A61F 2002/704* (2013.01); *A61F 2002/7625* (2013.01)

(56) References Cited

U.S. PATENT DOCUMENTS

| | | |
|---|---|---|
| 3,098,645 A | 7/1963 | Owens |
| 3,207,497 A | 9/1965 | Schoonover |
| 3,844,279 A | 10/1974 | Konvalin |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |
| 4,843,921 A | 7/1989 | Kremer |
| 4,865,376 A | 9/1989 | Leaver et al. |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,294,873 A | 3/1994 | Seraji |
| RE34,661 E | 7/1994 | Grim |
| 5,327,790 A | 7/1994 | Levin et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,885,809 A | 3/1999 | Ellenberger et al. |
| 5,888,212 A | 3/1999 | Petrofsky et al. |
| 5,898,948 A | 5/1999 | Kelly et al. |
| 5,910,720 A | 6/1999 | Williamson et al. |
| 5,932,230 A | 8/1999 | DeGrate |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,136,039 A | 10/2000 | Kristinsson |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janussen et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,945,947 B2 | 9/2005 | Ingimundarson et al. |
| 6,966,882 B2 | 11/2005 | Horst |
| 6,969,408 B2 | 11/2005 | Lecomte et al. |
| 6,992,455 B2 | 1/2006 | Kato et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Elnarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |

(56) References Cited

U.S. PATENT DOCUMENTS

| | | |
|---|---|---|
| 7,270,644 B2 | 9/2007 | Ingimundarson |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Elnarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgllsdottir et al. |
| 7,985,193 B2 | 7/2011 | Thorsteinsson et al. |
| 7,985,265 B2 | 7/2011 | Moser et al. |
| D643,537 S | 8/2011 | Lee |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,202,325 B2 | 6/2012 | Albrecht-Laatsch et al. |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |

(56) References Cited

U.S. PATENT DOCUMENTS

| | | |
|---|---|---|
| 2003/0195439 A1 | 10/2003 | Caselnova |
| 2004/0039454 A1 | 2/2004 | Herr |
| 2004/0049290 A1 | 3/2004 | Bedard |
| 2004/0054423 A1 | 3/2004 | Martin |
| 2004/0064195 A1 | 4/2004 | Herr |
| 2004/0088025 A1 | 5/2004 | Gesotti |
| 2004/0111163 A1* | 6/2004 | Bedard ............... A61F 2/644 623/33 |
| 2004/0181118 A1 | 9/2004 | Kochamba |
| 2005/0049652 A1 | 3/2005 | Tong |
| 2005/0059908 A1 | 3/2005 | Bogert |
| 2005/0070834 A1 | 3/2005 | Herr et al. |
| 2005/0085948 A1 | 4/2005 | Herr et al. |
| 2005/0155444 A1 | 7/2005 | Otaki et al. |
| 2006/0004307 A1 | 1/2006 | Horst |
| 2006/0069448 A1 | 3/2006 | Yasui |
| 2006/0094989 A1 | 5/2006 | Scott et al. |
| 2006/0135883 A1 | 6/2006 | Jonsson et al. |
| 2006/0173552 A1 | 8/2006 | Roy |
| 2006/0224246 A1 | 10/2006 | Clausen et al. |
| 2006/0249315 A1 | 11/2006 | Herr et al. |
| 2006/0258967 A1 | 11/2006 | Fujil et al. |
| 2006/0276728 A1 | 12/2006 | Ashihara et al. |
| 2007/0016329 A1 | 1/2007 | Herr et al. |
| 2007/0043449 A1 | 2/2007 | Herr et al. |
| 2007/0123997 A1 | 5/2007 | Herr et al. |
| 2007/0162152 A1 | 7/2007 | Herr et al. |
| 2008/0114272 A1 | 5/2008 | Herr et al. |
| 2008/0155444 A1 | 6/2008 | Pannese et al. |
| 2009/0030530 A1 | 1/2009 | Martin |
| 2009/0171469 A1 | 7/2009 | Thorsteinsson et al. |
| 2009/0222105 A1 | 9/2009 | Clausen |
| 2009/0259320 A1* | 10/2009 | Andrysek ............ A61F 2/64 623/24 |
| 2010/0025409 A1 | 2/2010 | Hunter |
| 2010/0114329 A1 | 5/2010 | Casler et al. |
| 2010/0179668 A1 | 7/2010 | Herr et al. |
| 2010/0312363 A1 | 12/2010 | Herr et al. |
| 2011/0224804 A1 | 9/2011 | Clausen et al. |
| 2011/0245931 A1 | 10/2011 | Clausen et al. |

FOREIGN PATENT DOCUMENTS

| | | |
|---|---|---|
| WO | WO-2004017872 | 3/2004 |
| WO | WO-2004019832 | 3/2004 |
| WO | WO-2006110895 | 10/2006 |
| WO | WO-2009082249 | 7/2009 |
| WO | WO-2010025409 | 3/2010 |
| WO | WO-2010027968 | 3/2010 |

OTHER PUBLICATIONS

Abbas J. and Chizeck H., "Neural Network Control of Functional Neuromuscular Stimulation Systems: Computer Simulation Studies," IEEE Transactions on Biomedical Engineering, vol. 42, No. 1, Nov. 1995, pp. 1117-1127.

Abul-haj, C. and Hogan, N., "Functional assessment of control systems for cybernetic elbow prostheses. Part I, Part II," IEEE Transactions on Biomedical Engineering, vol. 37, No. 11, Nov. 1990, Cambridge, MA, pp. 1025-1047.

Akazawa, K., et. al, "Biomimetic EMG prosthesis-hand," Proceedings of the 18th Annual International Conference of the IEEE Engineering in Medicine and Biology Society, vol. 2, Oct. 1996, Amsterdam, Netherlands, pp. 535-536.

Aminian, "Estimation of Speed and Incline of Walking Using Neural Network," IEEE Transactions on Biomedical Engineering, vol. 44 No. 3, Jun. 1995, pp. 743-746.

Anderson, F. and Pandy M., "Dynamic optimization of human walking," Journal of Biomechanical Engineering, vol. 123, Oct. 2001, pp. 381-390.

Andrews, et al., "Hybrid FES Orthosis incorporating closed loop control and sensory feedback," J. Biomed Eng., vol. 10, Apr. 1988, pp. 189-195.

Arakawa, T. and Fukuda, T., "Natural motion generation of biped locomotion robot using hierarchical trajectory generation method consisting of GA, EP layers," Proceedings of the 1997 IEEE International Conference on Robotics and Automation, Apr. 1997, Albuquerque, NM, pp. 211-216.

Au., et. al., "Powered Ankle-Foot Prosthesis for the Improvement of Amputee Ambulation," Proceedings of the 29th Annual International Conference of the IEEE, Aug. 2007, Lyon, France, pp. 3020-3026.

Au, S., "An EMG-position controlled system for an active ankle-foot prosthesis: an initial experimental study," Proc. of the 2006 IEEE International Conference on Rehabilitation Robotics, Jul. 2005, Chicago, IL, pp. 375-379.

Au, S. and Herr H., "Initial experimental study on dynamic interaction between an amputee and a powered ankle-foot prosthesis," Workshop on Dynamic Walking: Mechanics and Control of Human and Robot Locomotion, May 2006, Ann Arbor, MI, p. 1.

Au, S., et al. "An ankle-foot emulation system for the study of human walking biomechanics," Proc. of the 2006 IEEE Int. Conf. on Robotics and Automation, May 2006, Orlando, FL, pp. 2939-2945.

Au, S., et. al., "Biomechanical design of a powered ankle-foot prosthesis," Proc. of the 2007 IEEE Int. Conf. on Rehabilitation Robotics, Jun. 2007, Noordwijk, Netherlands, pp. 298-303.

Au, S., et. al., "Powered ankle-foot prosthesis to assist level-ground and stair-descent gaits," Neural Networks, vol. 21, No. 4, Mar. 2008, pp. 654-666.

Au, S., et. al., "Powered Ankle-foot Prosthesis Improves Walking Metabolic Economy," IEEE Trans. on Robotics, vol. 25, No. 1, Feb. 2009, pp. 51-66.

Barth, D., et. al., "Gait analysis and energy cost of below-knee amputees wearing six different prosthetic feet," Journal of Prosthetics & Orthotics, vol. 4, No. 2, Winter, 1992, pp. 63-75.

Baten, et al., "Inertial Sensing in Ambulatory back load Estimation," 18 Annual International Conferences of IEEE Engineering in Medicine and Biology Society, Amsterdam 1996, pp. 497-498.

Bateni, H. and Olney S., "Kinematic and kinetic variations of below-knee amputee gait," Journal of Prosthetics & Orthotics, vol. 14, No. 1, Mar. 2002, pp. 2-13.

Blaya, J. and Herr, H, "Adaptive control of a variable-impedance ankle-foot orthosis to assist drop-foot gait," IEEE Transactions on Neural Systems and Rehabilitation Engineering, vol. 12, No. 1, Mar. 2004, pp. 24-31.

Blaya, J.A., and Herr, H., "Adaptive Control of a Variable-Impedance Ankle-Foot Orthosis to Assist Drop Foot Gait," Artificial Intelligence Lab and Harvard-MIT Division Health Sciences and Technology, Boston, MA, 30 pages.

Blaya, J.A., et al., "Active Ankle Foot Orthoses (AAFO)," http://www.ai.mit.edu. Artificial Intelligence Laboratory, Massachusetts Institute of Technology, Cambridge, Massachusetts, 3 pages.

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003). 88 pages.

Blickhan, R., "The spring-mass model for running and hopping," J of Biomech. 22, Feb. 1969, Great Britain, pp. 1217-1227.

Bortz, "A New Mathematical Formulation for Strapdown Inertial Navigation," IEEE Transactions of Aerospace and Electronic Systems, vol. AES-7, No. 1, Jan. 1971, p. 61-66.

Brockway, J., "Derivation of formulae used to calculate energy expenditure in man," Human Nutrition Clinical Nutrition, vol. 41, Nov. 1987, pp. 463-471.

Brown, R., "On the nature of the fundamental activity of the nervous centres: together with an analysis of the conditioning of rhythmic activity in progression, and a theory of the evolution of function in the nervous system," J Physiol, vol. 48, No. 1. Mar. 1914, pp. 18-46.

Chang, et al., Ischemic Colitis and Complications of Constipation Associated with the use of Alosetron Under a Risk Management Plan: Clinical Characteristics, Outcomes, and Incidences The Americal Journal of Gastronenterology, vol. 105, No. 4, Apr. 2010, pp. 866-875.

Chu, A., Kazerooni, H. and Zoss, A., "On the Biomimetic Design of the Berkeley Lower Extremity Exoskeleton (BLEEX)," Proceed-

(56) References Cited

OTHER PUBLICATIONS ings of the 2005 IEEE International Conference on Robotics and Automation, Apr. 2005, Barcelona, Spain, pp. 4356-4363.

Colborne, G. R., S. Naumann, P. E. Langmuir, and D. Berbrayer, "Analysis of mechanical and metabolic factors in the gait of congenital below knee amputees," Am. J. Phys. Med. Rehabil., vol. 92, pp. 272-278, Oct. 1992.

Collins, et al., "Controlled Energy Storage and Return Prosthesis Reduces Metabolic cost of Walking," ASB 29th Annual Meeting, Cleveland, Ohio, Jul. 31-Aug. 5, 2005, 1 page.

Collins, et al., "Supporting Online Material for Efficient bipedal robots based on passivedynamic walkers," Mechanical Engineering, University of Michigan, Feb. 2005, Ann Arbor, MI, pp. 1-8.

Crago P., et. al., "New Control Strategies for neuroprosthetic systems," Journal of Rehabilitation Research and Development, vol. 33, No. 2, Apr. 1996, pp. 158-172.

Daley, M.A., Felix, G., Biewener, A. A., 2007. Running stability is enhanced by a proxirmadistal gradient in joint neuromechanical control. J Exp Bioi 210 (Pt 3), Nov. 2006, pp. 383-394.

Dapena, J. and McDonald, C., "Three-dimensional analysis of angular momentum in the hammer throw," Med. Sci. in Sports Exerc., vol. 21, No. 2, Apr. 1969, pp. 206-220.

Dietz, V., "Proprioception and locomotor disorders," Nat Rev Neurosci, vol. 3, Oct. 2002, pp. 781-790.

Dietz, V., "Spinal Cord Pattern Generators for Locomotion," download Feb 6, 2012, http://www.Clinph-journal.com/article/PIIS1388245703001202/fulltext, 12 pages.

Doerschuk, et. al., "Upper extremity limb function discrimination using EMG signal analysis," IEEE Transactions on Biomedical Engineering. vol. 30., No. 1., Jan. 1983, pp. 18-28.

Doke, J., et. al., "Mechanics and energetics of swinging the human leg," The Journal of Experimental Biology, vol. 208, Feb. 2005, pp. 439-445.

Dollar, et al., "Lower Extremity Exoskeletions and Active Orthoses; Challenges and State-of-the-Art," IEEE Transactions on Robotics, vol. 24, No. 1, Feb. 2008, 15 pages.

Donelan, J., et. al., "Force regulation of ankle extensor muscle activity in freely walking cats," J Neurophysiol, vol. 101, No. 1, Nov. 2008, pp. 360-371.

Donelan, J., et. al., "Mechanical work for step-to-step transitions is a major determinant of the metabolic cost of human walking," J. Exp. Biol., vol. 205, Dec. 2002, pp. 3717-3727.

Donelan, J., et. al. "Simultaneous positive and negative external mechanical work in human walking," Journal of Biomechanics, vol. 35, Jan. 2002, pp. 117-124.

Drake, C., "Ankle & Foot Splints or Orthoses," HemiHelp, Information Sheet 13 Last updated Jun. 2009, 5 pages.

Drake, C., "Ankle & Foot Splints or Orthoses (AFOs)," HemiHelp, Last updated Jun. 2009, 8 pages.

Drake, C., "Foot & Ankle Splints or Orthoses," HemiHelp Information Sheet, London, United Kingdon, 3 pages, www.hemihelp.org.uk/leaflets/hbleaflets90.htm.

Eilenberg, M., "A Neuromuscular-Model Based Control Strategy for Powered Ankle-Foot Protheses," Master's Thesis, Massachusetts Institute of Technology, Cambridge, Mass., 2009.

Ekeberg, O. and Grillner, S., "Simulations of neuromuscular control in lamprey swimming," Philos Trans R Soc Land B Bioi Sci, vol. 354, May 1999, pp. 895-902.

Ekeberg, O. and Pearson, K., "Computer simulation fo stepping in the hind legs of the cat: an examination of mechanisms regulating the stance-to-swing transition," J Neurophysiol, vol. 94, No. 6, Jul. 2005, pp. 4256-4268.

ENdo, K., et. al., "A quasi-passive model of human leg function in level-ground walking," Proc. of 2006 IEEE/RSJ International Conference on Intelligent Robots and Systems (IROS), Oct. 2006, Beijing, China, pp. 4935-4939.

Eppinger, S. Seering W., "Three dynamic problems in robot force control," IEEE Transactions on Robotics and Automation, vol. 8, No. 6, Dec. 1992, pp. 751-758.

Esquenazi, A. and DiGiacomo, R., "Rehabilitation After Amputation," Journ Am Podiatr Med Assoc, vol. 91, No. 1, Jan. 2001, pp. 13-22.

Farley, C. and McMahon, T., "Energetics of walking and running: insights from simulated reduced-gravity experiments," The American Physiological Society, Dec. 1992, pp. 2709-2712.

Farry, K. A., et al., "Myoelectric teleoperation of a complex robotic hand," IEEE Transactions on Robotics and Automation. vol. 12, No, 5, Oct. 1996, pp. 775-788.

Featherstone, R., 1987, "Robot Dynamic Algorithms", Boston, Mass., Kluwer Academic Publishers, pp. 155-172.

Fite, K., et. al., "Design and Control of an Electrically Powered Knee Prosthesis," Proc. of 2007 IEEE 10th International Conference on Rehabilitation Robotics (ICORR), Jun. 2007, pp. 902-905.

Flowers, W. "A Man-Interactive Simulator System for Above-Knee. Prosthetic Studies," Ph.D. thesis, Massachusetts of Institute Technology, Department of Mechanical Engineering, Jul. 10, 1973.

Fod, A., et. al., "Automated Derivation of Primitives for Movements Classification," Autonomous Robots, vol. 12, No. 1, Jan. 2002, pp. 39-54.

Frigon, A. and Rossignol, S., "Experiments and models of sensorimotor interactions during locomotion," Bioi Cybern, vol. 95, No. 6 Nov. 2006 pp. 607-627.

Fujita K, et. al., "Joint angle control with command filter for human ankle movement using functional electrical stimulation," Proc. of IEEE Ninth Annual Conference for the Engineering in Medicine and Biology Society, Nov. 1987, Boston, MA, pp. 1719-1720.

Fukuda, O. et al., "A human-assisting manipulator teleoperated by EMG signals and arm motions," IEEE Transactions on Robotics and Automation. vol. 19, No. 2, Apr. 2003, pp. 210-222.

Gates, D., "Characterizing ankle function during stair ascent, descent, and level walking for ankle prosthesis and orthosis design," Master's thesis, Boston University, 2004, pp. 1-82.

Geiritsen, K., et. al., "Direct dynamics simulation of the impact phase in heel-toe running," J. Biomech., vol. 28, No. 6, Jun. 1995, Great Britain, pp. 661-668.

Geyer, H., et. al., "Compliant leg behaviour explains the basic dynamics of walking and running " Proc. R. Soc. Cond. B 273, Aug. 2006, pp. 2861-2867.

Geyer, H., et. al., "Positive force feedback in bouncing gaits?," Proceedings of Royal Society B-Biological Sciences, vol. 270, No. 1529, Aug. 2003, pp. 2173-2183, 2003.

Geyer, H. and Herr H., "A muscle-reflex model that encodes principles of legged mechanics predicts human walking dynamics and muscle activities," IEEE Transactions on Neural Systems and Rehabilitations Engineering, vol. 18, No. 3, Jun. 2010, pp. 263-273.

Ghigliazza, R., et. al., "A simply stabilized running model," SIAM J. Applied. Dynamical Systems, vol. 2, No. 2, May 2004, pp. 187-218.

Godha, el al., "Integrated GPS/INS System for Pedestrian Navigation in a Signal Degraded Environment," ION GNSS, Sep. 2006, Fort Worth, TX, pp. 1-14.

Goswami, A., "Postural stability of biped robots and the foot-rotation indicator (FRI)point," International Journal of Robotics Research, vol. 18, No. 6, Jun. 1999, pp. 523-533.

Goswami, A. and Kallen, V., "Rate of change of angular momentum and balance maintenance of biped robots," Proceedings of the 2004 IEEE International Conference on Robotics and Automation, Apr. 2004, New Orleans, La., pp. 3785-3790.

Graupe, D., et al., "A microprocessor system for multifunctional control of upper-limb prostheses via myoelectric signal identification," IEEE TransactIon on Automatic Control. vol. AC-23, vol. 4, Aug. 1978, pp. 538-544.

Gregoire, L., and et al, "Role of mono- and bi-articular muscles in explosive movements,"International Journal of Sports Medicine 5, 614-630. Dec. 1984.

Grillner, S. and Zangger, P., "On the central generation of locomotion in the low spinal cat," Exp Brain Res, vol. 34, No. 2, Jan. 1979, pp. 241-261.

Grimes, D. L., "An active multi-mode above-knee prosthesis controller," Ph.D. Thesis, Massachusetts Institute of Technology, Jul. 20, 1979.

(56) References Cited

OTHER PUBLICATIONS

Gu, W., "The Regulation of Angular Momentum During Human Walking," Undergraduate Thesis, Massachusetts Institute of Technology, Physics Department, Jun. 2003, pp. 2-48.

Gunther, M., et. al., "Human leg design: optimal axial alignment under constraints," J. Math. Biol. vol. 48, Mar. 2004, pp. 623-646.

Gunther, M. and Ruder, H., "Synthesis of two-dimensional human walking; a test of the Amodel," Bioi. Cybern., vol. 89, May 2003, pp. 89-106.

Hanafusa et al., "A Robot Hand with Elastic Fingers and Its Application to Assembly Process," pp. 337-359, Robot Motion, Brady et al., MIT Press, Cambridge, MA, 1982.

Hansen, A. H., Childress, D. S., Miff, S.C., Gard, S. A., Mesplay, K. P., "The human ankle during walking: Implication for the design of biomimetic ankle prosthesis," Journal of Biomechanics, vol. 37, No. 10, Oct. 2004, pp. 1467-1474.

Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.

Heglund, N. "A Simple Design for a Force-Plat to Measure Ground Reaction Forces," J. Exp. Biol., vol. 93, Aug. 1981, pp. 333-338.

Herr, H. and McMahon, T.,"A trotting horse model," Int. J. Robotics Res., vol. 19, No. 6, Jun. 2000, pp. 566-581.

Herr, H. and Popvic, M., "Angular momentum regulation in human walking," J. Exp. Biol., vol. 211, Feb. 2006, pp. 467-481.

Herr, H. and Wilkenfeld A., "User-adaptive control of a magnetorheologicalprosthetic knee," Industrial Robot: An International Journal, vol. 30, No. 1, 2003, pp. 42-55.

Herr, H., et. al, "A model of scale effects in mammalian quadrupedal running," J Exp Biol 205 (Pt 7), Apr. 2002, pp. 959-967.

Heyn et al., "The Kinematice of the Swing Phase Obtained from Accelerometer and Gyroscope Measurements," 18th Annual International Conference of the IEEE Engineering in Medicine and Biology Society, Nov. 1996, Amsterdam, Netherlands, pp. 463-464.

Hill, V., "The heat of shortening and the dynamic constants of muscle," Proceedings of the Royal Society London B, vol. 126, No. 843, Oct. 1938, pp. 136-195.

Hirai, K., et al., "The development of Honda humanoid robot," Proceedings on IEEE/RSJ International Conference on Intelligent Robots and Systems, May 1998, Leuven, Belgium, pp. 1321-1326.

Hitt, J., R. Bellman, M. Holgate, T. Sugar, and K. Hollander, "The sparky (spring ankle with regenerative kinetics) projects: Design and analysis of a robotic transtibial prosthesis with regenerative kinetics," in Proc. IEEE Int. Conf. Robot. Autom., Orlando, Fla., pp. 2939-2945, Sep. 2007.

Hof. A., et. al., "Calf muscle moment, work and efficiency in level walking; role of series elasticity," Journal of Biomechanics vol. 16, No. 7, Sep. 1983, pp. 523-537.

Hofbaur, M. and Williams, B., "Hybrid Diagnosis with Unknown Behavioral Modes", Proceedings of the 13.sup.th International Workshop on Principles of Diagnosis (DX02), May 2002, pp. 1-10.

Hofbaur, M. and Williams, B., "Mode Estimation of Probabilistic Hybrid Systems", HSSC 2002, LNCS 2289, Mar. 25, 2002, pp. 253-266.

Hofmann, A., et. al., "A Sliding Controller for Bipedal Balancing Using Integrated Movement of Contact and Non-Contact Limbs," Proceedings of the IEEE/RSJ International Conference on Intelligent Robots and Systems, Sep. 2004, Sendai, Japan, pp. 1952-1959.

Hofmann, A., et. al., "Robust Execution of Bipedal Walking Tasks from Biomechanical Principles," Doctor of Philosophy at the Massachusetts Institute of Technology, Jan. 2006, 407 pages.

Hogan, N and Buerger S., "Impedance and Interaction Control," Robotics, and Automation Handbook, CRC Press, Jun. 2004, pp. 19.1-19.24.

Hogan, N. (1976) A review of the methods of processing EMG for use as a proportional control signal. Biomedical Engineering. pp. 81-86.

Hogan, N., "Impedance Control: An Approach to Manipulation: Part I—Theory," Journal of Dynamic Systems, Measurement, and Control, vol. 107, Mar. 1985, pp. 1-7.

Hogan, N., "Impedance Control: An Approach to Manipulation: Part II—Implementation, " Journal of Dynamic Systems, Measurement, and Control, 107:8-16, (1985).

Hogan, N., Impedance Control: An Approach to Manipulation: Part III—Application, Journal of Dynamics Systems, Measurement, and Control, 107:17-24, (1985).

Hogan, N., "Impedance Control: An Approach to Manipulation," Dept. of Mechanical Engineering and Laboratory of Manufacturing and Productivity, Massachusetts Institute of Technology, Cambridge MA, pp. 304-313, (Jun. 1984).

Hollander, K. W., T. G. Sugar, and D. E. Herring, "Adjustable robotic tendon using a 'Jack Spring' .TM.," Proceedings on IEEE International Conference on Rehabilitation Robotics, Chicago, pp. 113-118, Jun. 28, 2005.

Howard, "Joint and Actuator Design for Enhanced Stability in Robotic Force Control," Ph.D. thesis, Massachusetts Inst. of Technology, Dept. of Aeronautics and Astronautics, Sep. 19, 1990.

Huang, H. and Chen. C., "Development of a myoelectric discrimination system for a multi-degree prosthetic hand," Proceeding of the 1999 IEEE International Conference on Robotics and Automation, May 1999, Detroit, MI, pp. 2392-2397.

Huang, Q., "Planning walking patterns for a biped robot," IEEE Transactions on Robotics and Automation, vol. 17, No. 3, Jun. 2001, pp. 280-289.

Hultborn, H., Spinal reflexes, mechanisms and concepts: from Eccles to Lundberg and beyond, Prog Neuroblol, vol. 78, Feb. 2006, pp. 215-232.

Ijspeert, A. J., 2008, "Central pattern generators for locomotion control in animals and robots: a review," Neural Netw, vol. 21, No. 4, May 2008, pp. 642-653.

Ijspeert, A., et. al., "From swimming to walking with a salamander robot driven by a spinal cord model," Science, vol. 315, No. 5817, Mar. 2007, pp. 1416-1420.

International Search Report and Written Opinion for PCT/US2009/055600 dated Apr. 29, 2010 (23 pages).

International Search Report and Written Opinion for PCT/US2010/047279 dated Jan. 19, 2011 (11 pages).

International Search Report and Written Opinion for PCT/US2011/031105 dated Oct. 11, 2011 (16 pages).

International Search Report for PCT/US2012/020775 dated Jun. 1, 2012 (6 pages).

International Search Report for PCT/US2012/021084 dated Aug. 1, 2012 (3 pages).

International Search Report for PCT/US2012/022217 dated May 31, 2012 (6 pages).

Ivashko, D., et. al, "Modeling the spinal cord neural circuitry controlling cat hindlimb movement during locomotion," Neurocomputing, vol. 52-54, Mar. 2003, pp. 621-629.

Johansson, J., et al., "A clinical comparison of variable damping and mechanically passive prosthetic knee devices," American Journal of Physical Medicine & Rehabilitation, vol. 84, No. 8, Aug. 2005, pp. 563-575.

Johnson, C. and Lorenz R., "Experimental identification of friction and its compensation in precise, position controlled mechanisms," IEEE Trans. on Industry Applications, vol. 28, No. 6, Dec. 1992, pp. 1392-1398.

Jonic S, et. al., "Three machine learning techniques for automatic determination of rules to control locomotion," IEEE Trans Biomed Eng, vol. 46, No. 3, Mar. 1999, pp. 300-310.

Kadaba, M., et. al., "Measurement of lower extremity kinematics during level walking," J. Orthop. Res., vol. 8, May 1990, pp. 383-392.

Kadaba, M., et. al., "Repeatability of kinematic, kinetic, and electromyographic data in normal adult gait," J. Orthop. Res., vol. 7, Nov. 1989, pp. 849-860.

Kajita, K., et. al., "Biped walking on a low friction floor," Proceedings of the 2004 IEEE/RSJ International Conference on Intelligent Robots and Systems, Oct. 2004, Sendai, Japan., pp. 3546-3551.

(56) References Cited

OTHER PUBLICATIONS

Kajita, S., et. al., "A Hop towards Running Humanoid Biped," Proceedings of the 2004 IEEE International Conference on Robotics and Automation, Apr. 2004, New Orleans, La., pp. 629-635.

Kajita, S., et. al., "Resolved Momentum Control: Humanoid Motion Planning based on the Linear and Angular Momentum," Proceedings of the 2003 IEEE/RSJ International Conference on Intelligent Robots and Systems, Oct. 2003, Las Vegas, Nev., pp. 1644-1650.

Kaneko, K., et al., "Humanoid robot HRP-2," Proc. IEEE Int. Cont. on Robotics and Automation, Apr. 2004, New Orleans, La., pp. 1083-1090.

Kapti, A. and Yucenur M., "Design and control of an active artificial knee joint," Mechanism and Machine Theory, vol. 41, Apr. 2006, pp. 1477-1485.

Katie, D. and Vukobratovic, M., "Survey of intelligent control techniques for humanoid robots," Journal of Intelligent and Robotics Systems, vol. 37, Jun. 2003. pp. 117-141.

Kerrigan, D, et, al., "A refined view of the determinants of gait: significance of heel rise," Arch. Phys. Med. Rehab., vol. 81, Aug. 2000, pp. 1077-1080.

Kerrigan, D, et. al., "Quantification of pelvic rotation as a determinant of gait," Arch. Phys. Med. Rehab., vol. 82, Feb. 2001, pp. 217-220.

Khatib, O., et. al., "Coordination and decentralized cooperation of multiple mobile manipulators," Journal of Robotic Systems, vol. 13, No. 11, Nov. 1996, pp. 755-764.

Khatib, O., et. al., "Whole body dynamic behavior and control of human-like robots," International Journal of Humanoid Robotics, vol. 1, No. 1, Mar. 2004, pp. 29-43.

Kidder, et al., "A System for the Analysis of Foot and Ankle Kinematics During Gait," IEEE Transactions on Rehabilitation Engineering, vol. 4, No. 1, Mar. 1996, pp. 25-32.

Kim, et al., "Realization of Dynamic Walking for the Humaniod Robot Platform KHR-1," Advanced Robotics, vol. 18, No. 7, pp. 749-768, (2004).

Kirkwood C, et. al., "Automatic detection of gait events: a case study using inductive learning techniques.," J Biomed Eng, vol. 11, Nov. 1989, pp. 511-516.

Kitayama, I., Nakagawa N, Amemori K, "A microcomputer controlled intelligent A/K prosthesis," Proceedings of the 7th World Congress of the International Society for Prosthetics and Orthotics, Chicago. Jun. 28, 1992.

Klute, et al., Artificial Muscles: Actuators for Lower Limb Prostheses, Abstract in: Proceedings of the 2nd Annual Meeting of the VA rehabilitation Research and Development Service, Feb. 20-22, 2000, p. 107.

Klute, et al., "Artificial Muscles: Actuators for Biorobotic Systems," The International Journal of Robotics Research, vol. 21, No. 4, Apr. 2002, pp. 295-309.

Klute, et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.

Klute, et al., Intelligent Transtibial Prostheses with Muscle-Like Actuators,: 2002 American Physiological Society Intersociety Meeting: The Power of Comparative Physiology: Evolution, Integration, and Applied, 1 page.

Klute et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.

Klute, et al., "McKibben Artificial Muscles: Pneumatic Actuators with Biomechanical Intelligence," IEEE/ASME 1999 International Conference on Advanced Intelligent Mechatronlcs, Atlanta, GA, Sep. 19-22, 1999, pp. 221-226.

Klute, et al., "Muscle-Like Pneumatic Actuators for Below-Knee Prostheses," Actuator2000:7th International Conference on New Actuators, Bremen, Germany on Jun. 9-21, 2000, pp. 289-292.

Klute et al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., Oct. 1-3, 1998, p. 52.

Klute, et al., "Variable Stiffness Prosthesis for Transtibial Amputees," Dept of Veteran Affairs, Seattle, WA USA, 2 pages.

Klute, G., et. al., "Mechanical properties of prosthetic limbs adapting to the patient," Journal of Rehabilitation Research and Development. vol. 38, No. 3, May 2001, pp. 299-307.

Koganezawa, K. and Kato, 1., "Control aspects of artificial leg," IFAC Control Aspects of Biomedical Engineering, 1987, pp. 71-85.

Kondak, K. and Hommel, G., "Control and online computation of stable movement for biped robots," Proc. of the 2003 IEEE/RSJ International Conference on Intelligent Robots and Systems (IROS), Oct. 2003, Las Vegas, Nev., pp. 874-879.

Kostov A., et. al., "Machine learning in control of functional electrical stimulation (FES) systems for locomotion," IEEE Trans on Biomed Eng., vol. 42, No. 6, Jun. 1995, pp. 541-551.

Kuo, A., "A simple model of bipedal walking predicts the preferred speed-step length relationship," Journal of Biomechanical Engineering, vol. 123, Jun. 2001, pp. 264-269.

Kuo, A., "Energetics of actively powered locomotion using the simplest walking model," Journal of Biomechanical Engineering, vol. 124, Feb. 2002, pp. 113-120.

LaFortune, "Three-Dimensional Acceleration of the Tibia During Walking and Running," J. Biomechanics, vol. 24, No. 10, 1991, pp. 877-886.

LeBlanc, M. and Dapena, J., "Generation and transfer of angular momentum in the javelin throw," Presented at the 20th annual meeting of the American Society of Biomechanics, Oct. 1996, Atlanta, GA., pp. 17-19.

Li, C., et al. (Jun. 25, 2006) Research and development of the Intelligently-controlled prosthetic ankle joint. Proc. of IEEE Int. Conf. on Mechatronics and Automation. Luoyang, China, pp. 1114-1119.

Liu, X., Low, K. H., Yu, H. Y., Sep. 2004 'Development of a Lower Extremity Exoskeleton for Human performance Enhancement', IEEE Conf. on Intelligent Robots and Systems, Sendai, Japan.

Light, et. al., Skeletal Transients on Heel Strike in Normal Walking With Different Footwear. J. Biomechanics vol. 13, pp. 477-480.

Lloyd R. and Cooke C., "Kinetic changes associated with load carriage using two rucksack designs," Ergonomics, vol. 43, No. 9, Sep. 2000, pp. 1331-1341.

Luinge, "Inertial Sensing of Human Movement," Twente University Press, ISBN 9036518237, 2002, pp. 1-80.

Lundberg, A., Oct. 19, 1968. Reflex control of stepping. In: The Nansen memorial lecture V, Oslo: Universitetsforlaget, 5-42.

Macfarlane, P., "Gait comparisons for below-knee amputees using a flex-foot versus a conventional prosthetic foot," Journal of Prosthetics & Orthotics, vol. 3, No. 4, Summer, 1991, pp. 150-161.

Maganaris, C., "Force-length characteristics of in vivo human skeletal muscle," Acta Physiol. Scand., vol. 172, Aug. 2001, pp. 279-285.

Maganaris, C., "Force-length characteristics of the in vivo human gastrocnemius muscle," Clin. Anal., vol. 16, May 2003, pp. 215-223.

Martens, W.L.J., "'Exploring the Information Content and Some Applications of Body Mounted Piezo-Resistive Accelerometers," in: P.H. Veltink and R.C. van Lummel (eds.), Dynamic Analysis using Body Fixed Sensors, ISBN 90-9007328-0, 1994, pp. 8-11.

Maufroy, C., Towards a general neural controller for quadrupedal locomotion, Neural Netw, vol. 21, No. 4, Apr. 2008, pp. 667-681.

Mayagoitla R., el al., "Accelerometer and rate gyroscope measurement of kinematics: an inexpensive alternative to optical motion analysis systems," Journal of Biomechanics, vol. 35, Apr. 2002, pp. 537-542.

McFadyen, B. and Winter, D., "An integrated biomechanical analysis of normal stair ascent and descent," Journal of Biomechanics, vol. 21, No. 9, 1988, Great Britain, pp. 733-744.

McGeer T., "Passive Dynamic Walking," International Journal of Robotics, vol. 9, No. 2, May 1988, pp. 62-82.

McGeer, T., "Principles of walking and running," Advances in Comparative arid Environmental Physiology, vol. 11, Ch. 4, Apr. 1992, pp. 113-139.

(56) References Cited

OTHER PUBLICATIONS

Mcintosh, A., et. al., "Gait dynamics on an Inclined walkway," Journal of Biomechanics, vol. 39, Sep. 2005, pp. 2491-2502.

McMahon, T., "The mechanics of running: how does stiffness couple with speed?," J. of Biomecb., vol. 23, 1990, pp. 65-78.

McMahon, T., et. al., "Groucho Running," Journal of Applied Physiology, vol. 62, No. 6, Jun. 1987, pp. 2326-2337.

Minassian, K., et. al., "Human lumbar cord circuitries can be activated by extrinsic tonic input to generate locomotor-like activity," Hum. Mov. Sci., vol. 26, Mar. 2007 pp. 275-295.

Mochon, S., et. al., "Ballistic walking," Journal of Biomechanics, vol. 13, Dec. 1980, pp. 49-57.

Molen, N., "Energy/speed relation of below-knee amputees walking on motor-driven treadmill," Int. Z. Angew. Physio, vol. 31, Mar. 1973, pp. 173.

Morris, "Accelerometry—A Technique for the Measurement of Human Body Movements," J. Biomechanics, vol. 6, Nov. 1973, pp. 729-736.

Muraoka, T., et. al, "Muscle fiber and tendon length changes in the human vastus lateralis during slow pedaling," J. Appl. Physiol., vol. 91, Nov. 2001, pp. 2035-2040.

Nakagawa A., "Intelligent Knee Mechanism and the Possibility to Apply the Principle to the Other Joints," Proceedings of the 20th Annual International Conference of the IEEE Engineering in Medicine and Biology Society, Vo. 20, No. 5, Oct. 1998, pp. 2282-2287.

Neal R. and Hinton G., "A view of the EM algorithm that justifies incremental, sparse, and other variants," In Michael I. Jordan (editor), Learning in Graphical Models, 1999, Cambridge, MA, pp. 1-14.

Ng, et al., "Fuzzy Model Identification for Classification of Gait Events in Paraplegics," IEEE Transactions on Fuzzy Systems, vol. 6, No. 4, Nov. 1997, pp. 536-544.

Nielsen, D., et. al., "Comparison of energy cost and gait efficiency during ambulation in below-knee amputees using different prosthetic feel—a preliminary report," Journal of Prosthetics & Orthotics, vol. 1, No. 1, 1989, pp. 24-29.

Oda, T, Ketal., 2005, "In vivo length-force relationships on muscle fiver and muscle tendon complex in the tibialis anterior muscle." Int. J. Sport and Health Sciences 3, 245-252.

Ogihara, N. and Yamazaki, N., "Generation of human bipedal locomotion by a bio-mimetic neuro-musculo-skeietal model," Bioi Cybern, vol. 84, No. 1, Jan. 2001, pp. 1-11.

Palmer, M., "Sagittal plane characterization of normal human ankle function across a range of walking gait speeds," Master's Thesis, MIT, Feb. 2002, Cambridge, MA, pp. 1-71.

Paluska, D., and Herr, H., "Series Elasticity and Actuator Power Ouput," Proceedings of the 2006 IEEE International Conference on Robotics and Automation, May 2006, Orlando, FL, pp. 1830-1833.

Paluska, D., and Herr, H., "The effect of series elasticity on actuator power and work output: implications for robotic and prosthetic joint design," Robotics and Autonomous Systems, vol. 54, Jun. 2006, pp. 667-673.

Pang, M., et. al., "The initiation of the swing phase in human infant stepping: importance of hip position and leg loading," J Physiol, vol. 528, No. 2, Oct. 2000, pp. 389-404.

Pasch, K. A., and W. P. Seering, "On the drive systems for high performance machines," AMSE J. Mechanisms, Transmissions, and Automation in Design vol. 106, pp. 102-108, Mar. 1984.

Paul, C., et. al., "Development of a human neuro-musculo-skeletal model for investigation of spinal cord injury," Biol Cybern, vol. 93, No. 3, Aug. 2005, pp. 153-170.

Pearson, K., "Generating the walking gait: role of sensory feedback," Prog Brain Res, vol. 143, 2004, pp. 123-129.

Pearson, K., et. al., "Assessing sensory function in locomotor systems using neuro-mechanical simulations," Trends Neurosci, vol. 29, No. 11, Nov. 2006, pp. 625-631.

Perry, Gait Analysis: Normal and Pathological Function, New Jersey: SLACK Inc.; 1992, Book Review, 1 page.

Perry, J. and S. Shanfield, "Efficiency of dynamic elastic response prosthetic feet," Journal of Rehabilitation Research and Development, vol. 30, No. 1, 1993 pp. 137-143.

Petrofshy et al., "Feedback Control System for Walking in Man," Comput. Biol. Med., vol. 14, No. 2, Mar. 1984, pp. 135-149.

Pfeffer et al., "Experiments with a Dual-Armed, Cooperative, Flexible-Drivetrain Robot System," Proc. 1993 IEEE Int. Conf. on Robotics & Automation, vol. 3, pp. 601-608, May 5, 1993.

Popovic, et al., "Gait Identification and Recognition Sensor," Proceedings of 6th Vienna International Workshop on Functional Electrostimulation, Sep. 1998, pp. 1-4.

Popovic, D., "Control of Movement for the Physically Disabled," Springer-Verlag London Limited, May 2000, pp. 270-302.

Popovic D., et al., "Control Aspects of Active Above-Knee Prosthesis," Int. Journal Man-Machine Studies, (1991) 35, pp. 761-767.

Popovic, M., "Angular Momentum Primitives for Human Walking: Biomechanics and Control," Proc. of the 2004 IEEE/RSJ International Conference on Intelligent Robots and Systems, Sep. 2004, Sendai, Japan., pp. 1685-1691.

Popovic, M., et. al., "Angular Momentum Regulation during human walking: Biomechanics and Control," Proceedings of the 2004 IEEE International Conference on Robotics and Automation, Apr. 2004, New Orleans, LA, pp. 2405-2411.

Popovic, M., et. al., "Zero spin angular momentum control: definition and applicability," Proceedings of the IEEE-RAS/RSJ International Conference on Humanoid Robots, Nov. 2004, Los Angeles, CA, pp. 1-16.

Popovic, M., et. al., "Ground Reference Points in Legged Locomotion: Definitions, Biological Trajectories and Control Implications," International Journal of Robotics Research, Dec. 2006, pp. 79-104.

Popovic, M. and Herr, H., "Global Motion Control and Support Base Planning," Proceedings of the IEEE/RSJ International Conference on Intelligent Robots and Systems, Aug. 2005, Alberta, Canada, pp. 1-8.

Popovic, M.B., W. Gu and H. Herr, "Conservation of Angular Momentum in Human Movement," MIT AI Laboratory-Research Abstracts, Sep. 2002. pp. 231-232, 2002.

Pratt, G. and Williamson M., "Series elastic actuators," Proceedings on IEEE/RSJ International Conference on Intelligent Robots and Systems, Jan. 1995, Pittsburgh, PA, pp. 399-406.

Pratt, G., "Legged Robots: What's New Since Ralbert," IEEE Robotics and Automation Magazine, Research Perspectives, Sep. 2000, pp. 15-19.

Pratt, G., "Low Impedance Walking Robots," Integ. and Camp. Biol., vol. 42, Feb. 2002, pp. 174-181.

Pratt, J., et. al., "The RoboKnee: An Exoskeleton for Enhancing Strength and Endurance During Walking", IEEE Conf. on Robotics and Automation, Apr. 2004, New Orleans, LA, pp. 2430-2435.

Prochazka, A. and Yakovenko, S., "The neuromechanical tuning hypothesis," Prog Brain Res, vol. 165, Oct. 2007, pp. 255-265.

Prochazka, A. et. al., "Positive farce feedback control of muscles," J. of Neuro-phys., vol. 77, Jun. 1997, pp. 3226-3236.

Prochazka, A., et. al., "Sensory control of locomotion: reflexes versus higher-level control," Adv Exp Med Biol, vol. 508, 2002, pp. 357-367.

Ralbert, M., "Legged Robots that Balance," The MIT Press, Nov. 1986, Cambridge, MA, p. 89.

Ressler, D., et. al., "Length dependence of active force production in skeletal muscle," Journal Applied Physiology, vol. 86, Issue 5, May 1999, pp. 1455-1457.

Riener, R., et. al., "Stair ascent and descent at different inclinations," Gait Posture, vol. 15, Feb. 2002, pp. 32-44.

Reitman, et. al., Gait analysis in prosthetics: opinions, ideas and conclusions, Prosthetics and Orthotics International, 2002, 26, 50-57.

Robinson, D., "Design and an analysis of series elasticity in closed-loop actuator force control," Ph.D. Thesis, MIT, Jun. 2000, Cambridge, MA, pp. 1-123.

Robinson, D., "Series elastic actuator development for a biomimetic walking robot," Proceedings of IEEE/ASME International Conference on Advanced Intelligent Mechatronics, Sep. 1999, pp. 561-568.

(56) References Cited

OTHER PUBLICATIONS

Rosen, J., et al., 'A myosignal-based powered exoskeleton system,' IEEE Transactions on Systems, Man, and Cybernetics—Part A: Systems and Humans, vol. 31, No. 3, May 2001, pp. 210-222.

Rulna, A., et. al., "A collisional model of the energetic cost of support work qualitatively explains leg sequencing in walking and galloping, pseudo-elastic leg behavior in running and the walk-to-run transition," Journal of Theoretical Biology, vol. 237, Issue 2, Jun. 2005, pp. 170-192.

Rybak, I., et. al,, "Modelling spinal circuitry involved in locomotor pattern generation: insights from deletions during fictive locomotion," J Physiol. vol. 577 (Pt 2), Dec. 2001, 617-639.

Sanderson, D., et. al., "Lower extremity kinematic and kinetic adaptations in unilateral below-knee amputees during walking," Gait and Posture, vol. 6, No. 2, Oct. 1997, pp. 126-136.

Sanger, T., "Human arm movements described by a low-dimensional superposition of principal component," Journal of NeuroScience, vol. 20, No. 3, Feb. 2000, pp. 1066-1072.

Saranli, U., "RHex: A simple and highly mobile hexapod robot," Int. Jour. Rob. Res., vol. 20, No. 7, Jul. 2001, pp. 616-631.

Sarrigeorgldis K. and Kyriakopoulos K., "Motion control of the N.T.U.A. robotic snamek on a planar surface," Proc. of the 1998 IEEE International Conference on Robotics and Automation, May 1998, pp. 2977-2982.

Schaal, S., "Is imitation learning the route to humanoid robots?" Trends in Cognitive Sciences, vol. 3, Jun. 1999, pp. 233-242.

Schaal, S. and Atkeson, C., "Constructive incremental learning from only local information.," Neural Computation, vol. 10, No. 8, Nov. 1998, pp. 2047-2084.

Scott, S. and Winter, D., "Biomechanical model of the human foot: kinematics and kinetics during the stance phase of walking," J. Biomech., vol. 26, No. 9, Sep. 1993, 1091-1104.

Sentis, L., and O. Khatib, "Task-Oriented Control of Humanoid Robots Through Prioritization," IEEE-RAS/RSJ International Conference on Humanoid Robots, Nov. 2004, Santa Monica, CA, pp. 1-16.

Seyfarth, A., "Swing-leg retraction: a simple control model for stable running," J. Exp. Biol., vol. 206, Aug. 2003, pp. 2547-2555.

Seyfarth, A., et. al., "A movement criterion for running," J. of Biomech., vol. 35, May 2002, pp. 649-655.

Seyfarth, A., et. al., "Stable operation of an elastic three-segmented leg," Biol.Cybern., vol. 84, 2001, pp. 365-382.

Simon F., et. al, "Convergent force fields organized in the frog's spinal cord," Journal of NeuroScience, vol. 13, No. 2, Feb. 1993, pp. 467-491.

Sinkjaer, T., et. al., "Major role for sensory feedback in soleus EMG activity in the stance phase of walking in man," J Physiol, vol. 523, No. 3, Mar. 2000, pp. 817-827.

Skinner, H. and Effeney D., "Gait analysis in amputees," Am J Phys Med, vol. 64, Apr. 1986, pp. 82-89.

Smidt et al., "An Automated Accelerometry System for Gait Analysis," J. Biomechanics, vol. 10, 1977, pp. 367-375.

Srinivasan, M., "Energetics of legged locomotion: Why is total metabolic cost proportional to the cost of stance work," Proc. on ISB XXth Congress and the American Society of Biomechanics Annual Meeting, Jul. 2003, Cleveland, OH, pp. 829.

Stepien, J., et al., "Activity Levels Among Lower-Limb Amputees: Self-Report Versus Step Activity Monitor," Arch. Phys. Med. Rehabil., vol. 88, No. 7, Jul. 2007, pp. 896-900.

Sugano et al., "Force Control of the Robot Finger Joint equipped with Mechanical Compliance Adjuster," Proc. of the 1992 IEEE/RSJ Int. Conf. on Intel I. Robots & Sys., Jul. 1992, pp. 2005-2013.

Sugihara, T., et. al., "Realtime Humanoid Motion Generation through ZMP Manipulation based on Inverted Pendulum Control," Proceedings of the 2002 IEEE International Conference on Robotics and Automation, May 2002, Washington, DC, pp. 1404-1409.

Sup, F., "Design and Control of a Powered Transfemoral Prosthesis," The International Journal of Robotics Research, vol. 27, No. 2, Feb. 2008, pp. 263-273.

Taga, G., "A model of the neuro-musculo-skeletal system for human locomotion," Biol. Cybern., vol. 73, No. 2, Jul. 1995, pp. 97-111.

Takayuki "Biped Locomotion using Multiple Link Virtual Inverted Pendulum Model," Publication of Electronics Information and Systems Society, vol. 120, No. 2, Feb. 2000, 8 pages.

Thorough man, K. and R. Shadmehr, "Learning of action through adaptive combination of motor primitives," Nature, vol. 407, Oct. 2000, pp. 742-747.

Tomovic R. et al., "A Finite State Approach to the Synthesis of Bioengineering Control Systems," IEEE Transactions on Human Factors in Electronics, vol. 7, No. 2, Jun. 1966, pp. 65-69.

Tong, et al., "A Practical Gait Analysis System Using Gyroscopes," Medical Engineering & Physics, vol. 21, Mar. 1999, pp. 87-94.

Turker, K., "Electromyography: some methodological problems and issues," Physical Therapy, vol. 73, No. 10, Oct. 1993, pp. 698-710.

Van den Bogert, A., "Exotendons for assistance of human locomotion," Biomedical Engineering Online, Oct. 2003, pp. 1-8.

Van den Bogert, et al. "A Method for Inverse Dynamic Analysis Using Accelerometry," Journal Biomechanics, vol. 29, No. 7, 1996, pp. 949-954.

Veltink P., et al., "The Feasibility of Posture and Movement Detection by Accelerometry," D-7803-1377-1/93, IEEE, Oct. 1993, pp. 1230-1231.

Vukobratovic M. and Juricic, D., "Contributions to the synthesis of biped gait," IEEE Transactions on Biomedical Engineering, vol. BME-16, No. 1, Jan. 1969, pp. 1-6.

Vukobratovic M. and Stepanenko J., "Mathematical models of general anthropomorphic systems," Mathematical Biosciences, vol. 17, Aug. 1973, pp. 191-242.

Walsh, C., "Biomimetic Design of an Under-Actuated Leg Exoskeleton for Load-Carrying Augmentation," Master's Thesis, MIT, Feb. 2006, pp. 1-94.

Waters, RL., "Energy cost of walking amputees: the influence of level of amputation," J Bone Joint Surg., vol. 58, No. 1, Jan. 1976, pp. 42-46.

Wilkenfeld, A., "An Auto-Adaptive External Knee Prosthesis," Artificial Intelligence Laboratory, MIT, Sep. 2000, Cambridge, MA, pp. 1-3.

Wilkenfeld, A. J., "Biologically inspired auto adaptive control of a knee prosthesis," Ph.D. Thesis, Massachusetts Institute of Technology, Oct. 23, 2000.

Williamson, M., "Series Elastic Actuators," Artificial Intelligence Laboratory, MIT, Jan. 1995, Cambridg, MA, pp. 1-74.

Willemsen A., et al., "Automatic Stance-Swing Phase Detection from Accelerometer Data for Peroneal Nerve Stimulation," IEEE Transactions on Human Factors in Electronics, vol. 37, No. 12, Dec. 1990, pp. 1201-1208.

Willemsen A., et al., "Real-Time Gait Assessment Utilizing a New Way of Accelerometry," Journal of Biomechanics, vol. 23, No. 8, 1990, pp. 859-863.

Williams, B., "Mode Estimation of Model-based Programs: Monitoring Systems with Complex Behavior," Proceedings of the International Joint Conference on Artificial Intelligence, Aug. 2001, Seattle, WA, pp. 1-7.

Winter, D. A, "Energy generation and absorption at the ankle and knee during fast, natural, and slow cadences," Clinical Orthopedics and Related Research, vol. 175, May 1983, pp. 147-154.

Winter, D, and Robertson D. "Joint torque and energy patterns in normal gait," Biol. Cybern., vol. 29, May 1978, pp. 137-142.

Winter, D. and Sienko S., "Biomechanics of below-knee amputee gait," Journal of Biomechanics, vol. 21, No. 5, Aug. 1988, pp. 361-367.

Wisse, M., "Essentials of Dynamic Walking, Analysis and Design of two-legged robots," PhD Thesis, Technical University of Delft, 2004, pp. 1-195.

Woodward et al., "Skeletal Accelerations measured during different Exercises," Proceedings of the Institution of Mechanical Engineers, Part H: Journal of Engineering in Medicine, vol. 207, Jun. 1993, pp. 79-85.

Wu, The Study of Kinematic Transients in Locomotion Using the Integrated Kinematic Sensor, IEEE Transactions on Rehabilitation Engineering, vol. 4, No. 3, Sep. 1996, p. 193-200.

(56) References Cited

OTHER PUBLICATIONS

Yakovenko, S., et. al., "Contribution of stretch reflexes to locomotor control: a modeling study," Biol Cybern, vol. 90, No. 2, Jan. 2004, pp. 145-155.
Yun X., "Dynamic state feedback control of constrained robot manipulators," Proc. of the 27th conference on Decision and Control, Dec. 1986, pp. 622-626.
Zlatnik, D., et. al., "Finite-state control of a trans-femoral prosthesis," IEEE Trans. on Control System Technology, vol. 10, No. 3, May 2002, pp. 408-420.
U.S. Appl. No. 13/347,443, filed Jan. 10, 2012, Zhixiu Han.
U.S. Appl. No. 13/356,230, filed Jan. 23, 2012, Zhixiu Han.
U.S. Appl. No. 13/417,949, filed Mar. 12, 2012, Hugh M. Herr.

* cited by examiner

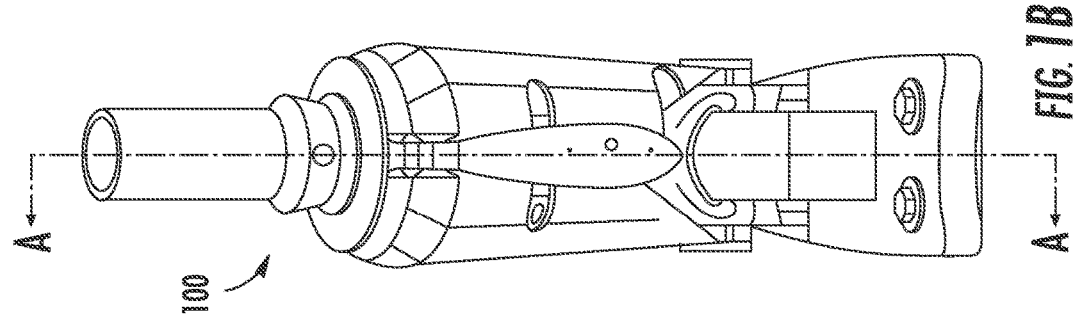
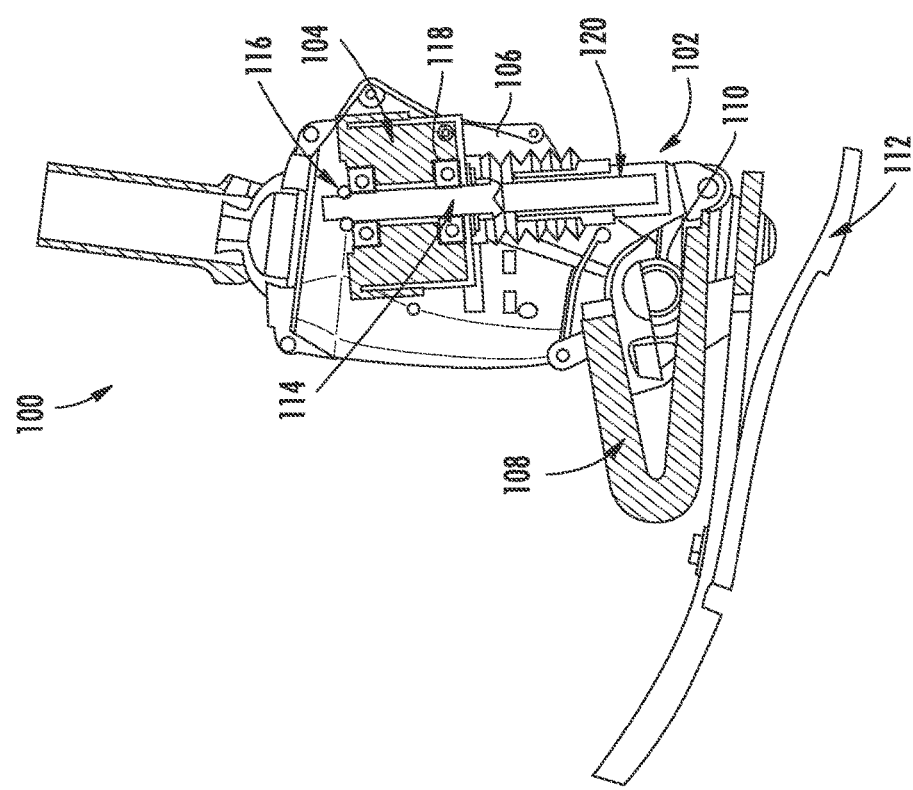

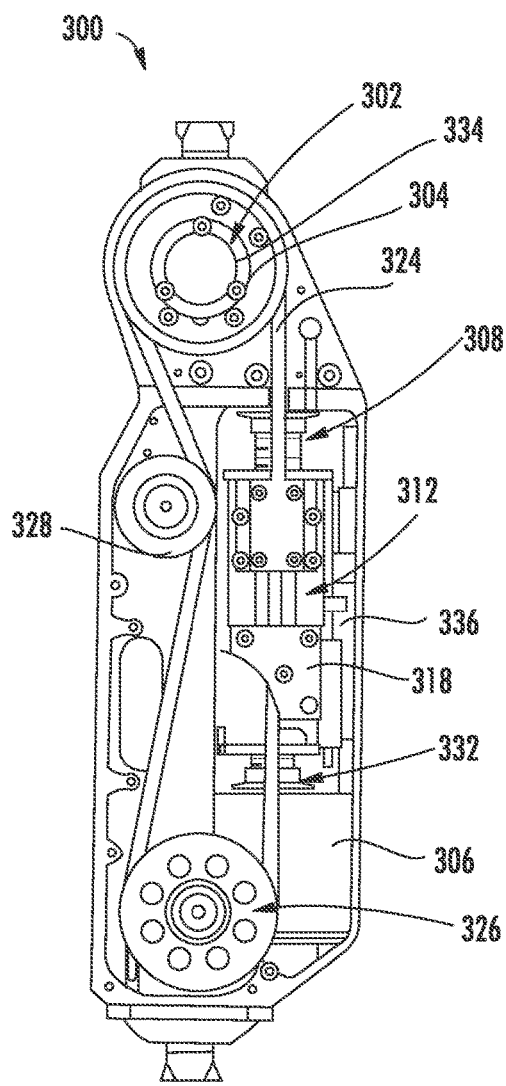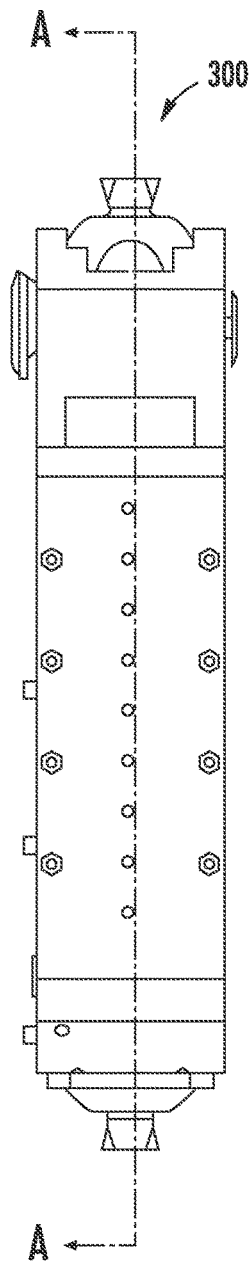
FIG. 3A
FIG. 3B

TABLE 1: DESIGN AND OPERATION PARAMETERS

| PARAMETER | MINIMUM | TYPICAL | MAXIMUM | UNIT |
|---|---|---|---|---|
| PEAK ACTUATOR TORQUE WITHIN A GAIT CYCLE | 0.25 | 1.5 | 2.5 | NM/KG@(0.75, 1.25, 3.5 M/SEC) |
| JOINT VELOCITY | 1 | 2 | 3 | RAD/SEC |
| SEA FIRST RESONANCE | 12 | 50 | 100 | HZ |
| MOTOR DISSIPATION CONSTANT, $\frac{R}{K_t^2}$ ACROSS GEAR RATIO RANGE | 2 | 6 | 50 | WATTS/(NM)$^2$ |
| ACTUATOR WEIGHT | | 5.2 | | G/KG |
| TRANSMISSION GEAR (REDUCTION) RATIO | 15 | 40 | 80 | |
| BALL-SCREW PITCH | 3 | 6 | 12 | MM |
| SERIES STIFFNESS (SPRING CONSTANT) AT MAXIMUM MECHANICAL POWER AMPLIFICATION | 3.0 | 4 | 4.5 | NM/RAD/KG |
| PARALLEL STIFFNESS (SPRING CONSTANT) | | 5 | | NM/RAD/KG |
| WEIGHT OF THE WEARER | 90 | 220 | 350 | LB. |

FIG. 5

BIOMIMETIC JOINT ACTUATORS

CROSS REFERENCE TO RELATED APPLICATIONS

This application is a Divisional of U.S. patent application Ser. No. 13/417,949, filed Mar. 12,2012, which claims priority to and the benefit of U.S. Provisional Patent Application Ser. No. 61/451,887, filed on Mar. 11, 2011, the contents of which are hereby incorporated by reference herein in their entirety.

FIELD OF THE INVENTION

This invention relates generally to powered human, augmentation devices, such as lower-extremity prosthetic, orthotic, or exeskefton apparatus, and/or to humanoid robotic devices designed to emulate haroan biomechanics and to normalize function and, in particular, to device components that deliver mechanical power, and methods for controlling such components.

BACKGROUND

Superior biomimetic, lower-extremity augmentation systems and humanoid systems generally modulate mechanical impedance, joint equilibrium, and torque in accordance with gait cycle phase, walking speed, and/or terrain in a way that can emulate human behavior. In so doing, such systems can normalize or even augment metabolic cost-of-transport and self-selected walking speed with respect to average limb/joint function in a typical human. Some powered prosthetic, orthotic, and exoskeletal devices for providing and/or augmenting human joint function such, that at least a biomimetic joint response is achieved have been described in co-pending U.S. patent application Ser. No. 12/157,727 "Powered Ankle-Foot Prosthesis" filed on Jun. 12, 2008 (Publication No. US201/0257764 A1); co-pending U.S. patent application Ser. No. 12/552,013 "Hybrid Terrain-Adaptive Lower-Extremity Systems" filed on Sep. 1, 2009 (Publication No. US2010/0179668 A1): co-pending U.S. patent application Ser. No. 13/079564 "Controlling Power in a Prosthesis or Orthosis Based on Predicted Walking Speed or Surrogate for Same" filed on Apr. 4, 2011; co-pending U.S. patent application Ser. No. 13/079571 "Controlling Torque in a Prosthesis or Orthosis Based on a Deflection of Series Elastic Element" filed on Apr. 4, 2011; co-pending U.S. patent application Ser. No. 13/347443 "Powered joint Orthosis" filed on Jan. 10, 2012; co-pending U.S. patent application Ser. No. 13/356230 "Terrain Adaptive Powered Joint Orthosis" filed on Jan. 23, 2012; and co-pending U.S. Provisional Patent Application Ser. No. 61/595453 "Powered Ankle Device" filed on Feb. 6, 2012, the disclosures of ail of which are hereby incorporated herein in their entireties.

In these devices the torque, the impedance, and joint equilibrium are generally controlled in each joint to provide at least a biomimetic response to a wearer of the device. Specifically, these devices may provide torque in advance of toe off during a gait cycle to propel the joint. This can enable the wearer to walk faster and with less effort while at the same time improving gait mechanics, thereby mitigating the wearer's discomfort.

A series-elastic actuator (SEA), described in the above-referenced patent applications, can be used to create a backdrivable joint mechanism, in prosthetic, orthotic, exoskeleton, and/or humanoid devices in which both force (torque) and impedance are controlled. Specifically, in various lower-extremity devices described in these patent applications, the SEA typically emulates the muscle-tendon unit response in an ankle, knee or hip device, specifically through implementation of a positive force or velocity feedback controller that mimics a characteristic reflex response of the joint. To this end, the SEA typically stores energy in one phase of a gait cycle (e.g., in the controlled dorsiflexion phase for an ankle device) and releases the stored energy later in the gait cycle (e.g., in the powered plantar flexion phase in the ankle device). Thus, the SEA may amplify the peak power of the actuator, thereby reducing the size and weight of the motor and the transmission. As such, devices employing an SEA may both require less battery power and produce less acoustic noise than other robotic systems that provide torque for propelling a joint, but that do not use an SEA. Nevertheless, the devices using an SEA (as well as those not using an SEA) can still require substantial battery power and may produce noise that is unacceptable to some users in certain situations.

One of the reasons for the high power consumption and noise is that conventional electric actuators in leg prosthetic, orthotic, and exoskeletal devices generally employ low-torque, high-speed (i.e., high revolutions per minute (RPM)) motors that are light weight but are limited in their torque capability. For example, the EC-4Pole 30 Maxon Motor that may be employed in prosthetic and/or orthotic devices has a low-mass (about 300 grams), but has a rather modest torque capability of about 0.12 Newton-meter continuous torque, and a relatively high speed (about 16,500 RPM zero-load speed). To achieve the high joint torque and low speed required to emulate the dynamics of a biological leg joint using a low torque, high RPM motor, a transmission haying a large reduction ratio (e.g., greater than about 150:1) is generally needed. Transmissions having such high reduction ratios, when used in an actuator system to emulate the biological dynamics of ankle, knee, and/or hip joints, typically produce significant acoustic noise output. Such transmissions may also have large frictional losses and may have low backdrivability.

A high acoustic output may draw attention to the wearer of the device, and can thus be uncomfortable or embarrassing in certain social situations. Moreover, high friction and poor backdrivability can result in a relatively poor transmission efficiency, increasing the power consumption of the device. These two parameters can also adversely affect the overall control of the joint, whether for adjusting the joint position or for applying impedance and/or force/torque. In addition, high transmission ratios can be difficult to achieve and often require many functional parts, which limits system cycle life and increases manufacturing complexities and associated, costs. Therefore, there is a need for improved powered actuators for use in prosthetic, orthotic, exoskeleton, and/or humanoid devices.

SUMMARY

In various embodiments, the present invention provides powered actuator devices and methods for operating/controlling such actuators so that human augmentation devices using these actuators can accurately modulate the torque, joint equilibrium, and impedance applied to a human pint, while significantly reducing the power consumption and acoustic noise of the powered actuators. This is achieved, in part, by using a high torque, low RPM motor that is directly coupled to a highly backdrivable, low friction, low-reduction ratio transmission, and by using an elastic element, coupled in series with the transmission, coupling the joint to which torque/impedance is to be supplied with the transmission.

Conventional actuators typically employ high-rpm motors and high gear-ratio transmissions using timing belts and gears, which can generate acoustic noise and dissipate power. In various powered actuators described herein, an efficient, high-torque motor, such as a transverse flux motor, having low thermal dissipation is coupled directly to a low gear-ratio transmission, e.g., a transmission having a reduction ratio of about 80:1 or less. Examples of such transmissions include ball-screw and cable transmissions. These actuators are thus directly coupled to the robotic joint, via an elastic element coupled in series with the low-reduction transmission, delivering high-torque with low inertia and high efficiency to the joint. As these actuators eliminate the belts and gears med in conventional transmissions, they can be more durable, light-weight, quiet, backdrivable, powerful, efficient, and scalable, compared to the conventional actuators.

These improved SEAs may be employed to emulate the behavior of human muscles and tendons. In general, low acoustic noise, force and impedance controllability, and high efficiency are important attributes of biological muscle-tendon units. An SEA including a high torque, low RPM motor (e.g., a transverse-flux motor), a low-reduction ratio transmission directly coupled to the motor, and tendon-like elastic element coupled in series with the transmission can provide many of these attributes of biological muscle-tendon units with greater efficacy compared to traditional actuator designs currently employed in wearable robotic systems. This particular combination of mechanical and electromechanical elements in the improved SEAs facilitates a biomimetic actuator platform capable of emulating the natural dynamics of biological leg joints in tasks such as walking, stair climbing/descending, and running, at high efficiency and controllability with relatively low acoustic noise output.

Accordingly, in one aspect, embodiments of the invention feature a powered actuator for supplying one or more of an augmentation torque, joint equilibrium, and an impedance to a joint augmented by a powered human augmentation device. The powered actuator includes a motor having a dissipation constant less than about 50 W/(Nm)$^2$, and a transmission coupled directly to the motor. The powered actuator also includes an elastic element coupled to the joint that is also coupled, in series, to the transmission. The powered actuator, as adapted for use in an ankle, can generate a normalized, joint torque in a range from about −2.8 to about 2.8 Nm/kg.

In some embodiments, the motor may include a high-torque motor supplying motor torque of at least about 0.06 Nm/kg. Alternatively, or in addition, the motor may include a low revolutions per minute (RPM) motor having an RPM less than about 1500, a transverse-flux motor, or both. The actuator may be adapted to fee backdrivable.

In some embodiments, the transmission has a gear ratio less than about 80:1. The transmission may include a ball-screw transmission having a bah nut coupled to the elastic element, The ball-screw transmission may include a screw having a pitch in a range of about 2 mm up to about 10 mm, which can yield the gear ratio of less than about 80:1.

In some embodiments, the elastic element may include a spring, and the powered actuator may additionally include a cable and a joint output pulley. In those embodiments, the cable Is coupled to both the spring and the joint output pulley. In some other embodiments, the transmission includes a ball-screw transmission having a ball nut coupled to the motor rotor and the screw is coupled to the elastic element.

In some embodiments, the motor of the powered actuator includes a motor having an external rotor, and the transmission includes a cable and a joint output pulley. The cable couples the external rotor and the joint output pulley. The cable may be any one of a synthetic cable, a steel cable, a belt, and a chain.

The powered actuator may also include a motor encoder adapted, to measure angular displacement of a rotor of the motor with respect to a stator of the motor, and a joint encoder adapted to measure angular displacement of the joint about a joint pivot. The motor encoder, the joint encoder, or both may include an absolute encoder, The motor encoder and/or the joint encoder may also include a magnetic encoder having at least 13-bit resolution.

In another aspect (as shown in FIG. 6), embodiments of the invention feature a method for augmenting joint function using a powered human augmentation device. The method includes modulating one or more of joint. augmentation torque, joint impedance, and joint equilibrium during a phase of a gait cycle. The modulation is achieved, in part, using a motor having a dissipation constant less than about 50 W/(Nm)$^2$ and that is coupled directly to a transmission. The transmission is serially coupled to an elastic element that is coupled to the joint. The method includes energizing the motor (block 602) to apply the augmentation torque (block 604) to the joint during a phase of the gait cycle, such that the applied torque normalized by weight is in a range from about −2.8 Nm/kg up to about 2.8 Nm/kg. The transmission may have a gear ratio less than about 80:1.

In some embodiments, the method includes energizing the motor to apply stiffness (a component of the impedance) to the joint (block 618), so that energy is stored in the elastic element and power from release of the stored energy combines with the applied motor power to achieve a positive torque feedback response that approximates a muscle-tendon reflex. The method may also include energizing the motor to apply the torque to achieve a desired joint equilibrium, and subsequently shorting leads of the motor during a stance phase of the gait cycle to approximate a mechanical clutch, such, that the joint equilibrium is substantially maintained during a portion of the stance phase (block 616).

In some embodiments, the method includes measuring angular displacement of a rotor of the motor with respect to a stator of the motor (block 606) and measuring angular displacement of a structure with respect to the joint (block 608). The method also includes determining a state of the elastic element based, at least in part, on both the angular displacement of the rotor and the angular displacement of the structure (block 610). Moreover, based at least in part on the state of the elastic element and the angular displacement on the motor torque contribution of the motor is computed (block 612), and the modulation is adjusted (block 614), based at least in part on the computed contribution of the motor torque.

In another aspect, embodiments of the invention feature a method for supplying one or more of an augmentation torque, joint equilibrium, and an impedance to a joint augmented by a powered human augmentation device. The method includes directly coupling a motor having a dissipation constant less than about 50 W/(Nm)$^2$ to a transmission. The method also includes coupling an elastic element to both the joint and the transmission, whereby when the motor is energized to supply the augmentation torque, the torque applied to the joint normalized by weight is in a range from about −2.8 Nm/kg up to about 2.8 Nm/kg.

In some embodiments, the motor may include a high-torque motor supplying torque of at least about 0.06 Nm/kg. Alternatively, or in addition, the motor may include a low revolutions per minute (RPM) motor having an RPM less than about 1500, a transverse-flux motor, or both. The actuator may be adapted to be backdrivable.

In some embodiments, the transmission has a gear ratio less than about 80:1. The transmission may include a ball-screw transmission having a ball nut coupled to the elastic element. The ball-screw transmission may include a screw having a pitch in a range of about 2 mm up to about 10 mm, which can yield the gear ratio of less than about 80:1.

In some embodiments, the elastic element may include a spring, and the powered actuator may additionally include a cable and a joint output pulley. In those embodiments, the cable is coupled to both the spring and the joint output pulley. In some other embodiments, the transmission includes a ball-screw transmission having a ball nut coupled to the motor rotor and the screw is coupled to the elastic element.

In some embodiments, the motor of the powered actuator includes a motor having an external rotor, and the transmission includes a cable and a joint output pulley. The cable couples the external rotor and the joint output pulley. The cable may be any one of a synthetic cable, a steel cable, a belt, and a chain. The augmentation torque and/or the impedance may supplied to one or more of a hip joint, a knee joint, and an ankle joint.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations. As used herein, the term, "substantially" means about ±10% and, in some embodiments, about ±5%.

BRIEF DESCRIPTION OF THE DRAWINGS

In the drawings, like reference characters generally refer to the same parts throughout the different views. Also, the drawings are not necessarily to scale, emphasis instead, generally being placed upon illustrating the principles of the invention. In the following description, various embodiments of the present invention are described with reference to the following drawings, in which:

FIGS. 1A-1C illustrate a powered actuator employing a ball-screw transmission, according to one embodiments for use with ankle prostheses;

FIGS. 3A-3C illustrate a powered actuator employing a ball-screw transmission, according to one embodiment, for use with knee prostheses;

FIG. 5 is a table of certain, design, and operating parameters of powered, actuators according to various embodiments.

DESCRIPTION

Figure 1C:
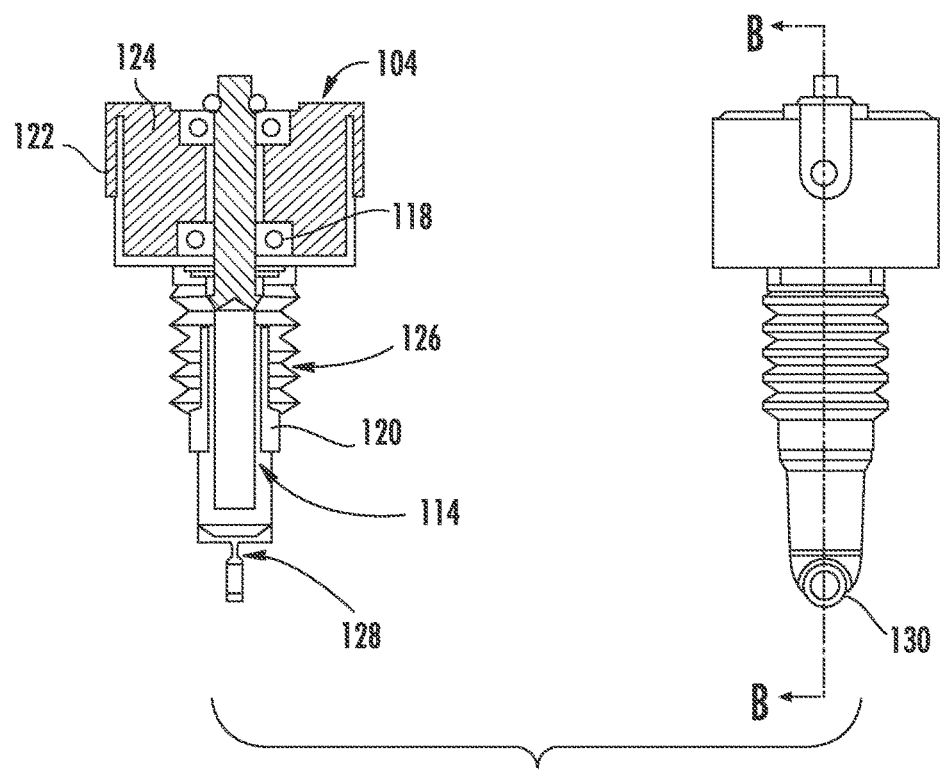

The entire contents of each of U.S. patent application Ser. No. 12/157,727 "Powered Ankle-Foot Prosthesis" filed on Jun. 12, 2008 (Publication No. US2011/0257764 A1); U.S. patent application Ser. No. 12/552,013 "Hybrid Terrain-Adaptive Lower-Extremity Systems" filed on Sep. 1, 2009 (Publication No. US2010/0179668 A1); U.S. patent application Ser. No. 13/079564 "Controlling Power in a Prosthesis or Orthosis Based on Predicted Walking Speed, or Surrogate for Same" filed on Apr. 4, 2011; U.S. patent application Ser. No. 13/079571 "Controlling Torque in a Prosthesis or Orthosis Based on a Deflection of Series Elastic Element" filed on Apr. 4, 2011; U.S. patent application Ser. No. 13/347443 "Powered Joint Orthosis" filed on Jan. 10, 2012; co-pending U.S. patent application Ser. No. 13/356230 "Terrain Adaptive Powered Joint Orthosis" filed on Jan. 23,2012; and co-pending U.S. Provisional Patent Application Ser. No. 61/595453 "Powered Ankle Device" filed On Feb. 6. 2012 are incorporated herein by reference.

In various embodiments described below, the use of an SEA in a biomimetic ankle device is described for the sake of convenience. That SEA mechanism can be readily adapted for use with biomimetic knee and/or hip devices also, A biomimetic ankle-foot prosthesis 100 depicted in FIGS. 1A and 1B includes an SEA 102. The SEA 102 uses a direct-drive, ball-screw based transmission system in which an electric motor 104 is directly coupled to a ball-screw transmission 106, which is serially coupled to an elastic element 108. connecting the transmission 106 to a joint output, i.e., the ankle pivot 110. Thus, the SEA 102 applies torque via a robotic joint, i.e., the ankle pivot 110, to an output load, i.e., a carbon-fiber foot 112. In some embodiments, another elastic element may be connected, between the motor 104 and the foot 112, in parallel to the serially connected elastic element 108.

The motor 104 is a high-torque, low-speed (rpm) motor, e.g., a transverse-flux motor, an "external rotor" permanent magnet motor, etc. Modern transverse-flux motors employ a high-pole-count external rotor (internal stator) and circumferentially-applied stator windings to achieve high-torque density with low winding resistance, thereby mitigating many of the typical disadvantages of using other high-torque motors in portable devices. These transverse flux motors are particularly suited for prosthetic/orthotic/exoskeletal/humanoid devices because they have a high power-to-weight ratio. Transverse flux motors also have lower peak-to-continuous power ratings compared to those of other motors, thereby enabling a prosthetic/orthotic/exoskeletal device to operate at high power levels for longer periods without reaching thermal limits. Transverse flux motors can also provide a significant motor dissipation reduction as defined by the motor copper loss per square; unit of torque as defined by $R/k_t^2$, whereby R is the stator winding resistance in ohms, and $k_t$ is the motor torque constant measured in N-m/amp., thereby increasing motor efficiency. Lower Motional losses (generally due to the reduced number of motor revolutions per gait cycle) in the transmission further increase the overall efficiency of the prosthetic/orthotic/exoskeletal devices. The design life of the transmission can increase also, in part due to the reduction in motor revolutions per cycle. These benefits can be leveraged by the SEAs, such as the SEA 102, using ball-screw and cable transmissions.

Specifically, the rotor of the motor 104 is attached to a ball-screw shaft 114 using a clamping nut 116. The clamping nut applies a preload to the axial thrust hearings 118 that serve to align the ball-screw shaft 114 radially and support the thrust imparted by the ball nut 120 during actuation. The rotating screw 114 drives the ball-nut 120 longitudinally which in turn drives the series spring 108 about the ankle pivot bearings 110, thus providing impedance and/or torque at the ankle to the foot 112. Those skilled in the art appreciate that alternatively, in some embodiments, the rotor can be directly coupled to the ball-nut, thereby controlling the linear translation of the screw.

Typically in an ankle, device, during the controlled dorsiflexion phase of the gait cycle, the SEA 102 delivers a programmable impedance and joint equilibrium at the ankle joint, it should be understood that in other devices, such as hip and/or knee devices, the SEA may deliver a programmable impedance, joint equilibrium, and/or torque in the controlled dorsiflexion and/or other phases of the gait cycle. In the ankle device 100, the SEA 102 thus emulates a non-linear (hardening) torsional spring impedance of the ankle pivot 110; the associated torque is stored as potential energy in the series spring 108, The hardening spring behavior can be accomplished through, use of non-linear positive force or velocity feedback (as described in the various co-pending patent applications identified above) as a means of emulating the calf-muscle/Achilles tendon reflex response. At or near the end of the controlled dorsiflexion phase, the SEA 102 applies torque and, as the foot heel, begins to lift off a surface on which the wearer is walking, the energy stored in the series spring 108 is released, like a catapult combining with the motor applied torque to produce a positive force/torque feedback response to approximate a muscle-tendon reflex, thus producing at least a biomimetic response. The impedance and/or torque applied by the motor 104 may be normalized by the wearer's weight.

An absolute encoder may be used to measure angular displacement of the motor rotor in relation to the staler, Another absolute encoder may be used to measure angular displacement of the foot structure 112 about the ankle pivot bearings 110. Instead of absolute encoders, magnetic field angle encoders, e.g., the RMB-20 having a 13-bit resolution, manufactured by Renishaw, may be used. The measured angular displacements can be used to determine the state of the motor 104, for the purposes of commutation, torque, and/or joint equilibrium control, and of the output joint, i.e., ankle pivot 110. These motor and ankle states can be used to estimate the state of the series spring 108. (See for example, the co-pending U.S. patent application Ser. No. 13/079564 "Controlling Power in a Prosthesis or Orthosis Based on Predicted Walking Speed or Surrogate for Same" filed on Apr. 4, 2011; U.S. patent application Ser. No. 13/079571 "Controlling Torque in a. Prosthesis or Orthosis Based on a Deflection of Series Elastic Element." filed on Apr. 4, 2011). In general, the motor position defines a joint equilibrium position through simple kinematics (e.g., the law of cosines). The difference between that joint equilibrium position and the actual joint position, when, multiplied by a calibrated series spring constant, determines the series spring torque and, thereby, the energy stored in the spring.

In some embodiments, based on the determined series spring state and stiffness (i.e., spring constant) of the series spring 108, force and joint torque contribution of the SEA 102 is determined. Furthermore, based on the determined contribution of the spring force and motor torque, the torque and impedance applied by the SEA 102 and equilibrium of the joint can be modulated, (See for example, the co-pending U.S. patent application Ser. No. 13/347443 "Powered Joint Orthosis" filed on Jan. 10, 2012; co-pending U.S. patent application Ser. No. 13/356230 "Terrain Adaptive Powered Joint Orthosis" filed on Jan. 23, 2012; and co-pending U.S. Provisional Patent Application Ser. No. 61/595453 "Powered Ankle Device" filed on Feb. 6, 2012).

The SEA 102 can achieve a low gear ratio, i.e., a ratio of the motor rotor displacement and the output joint displacement that is less than about 30:1 or about 20:1. In one embodiment of the SEA 102, the ball-Screw 114 typically delivers over about 2600 N of axial force at a screw pitch of 12 mm, delivering over 100 Nm of torque to the foot structure 112. A dissipation constant of the motor 104 across a range of gear ratios (e.g., from about 15:1 up to about 80:1) is less than about 50 Watts/(Nm)$^2$. The motor dissipation, constant is a ratio of the total resistance R of the windings of the motor rotor and square of torque output by the motor per unit current supplied to the motor, denoted as $k_t^2$.

In general, the torque output of a motor increases with the current drawn by the motor, which is related to the power supplied to the motor. However, the portion of the supplied power that is lost and dissipated as heat is proportional to the square of the current drawn by the motor. Therefore, as more power is supplied to a motor, the fraction of that power that increases the torque output of the motor can be less than the fraction that is wasted in the form of heat dissipation. Therefore, the motor 104, which has a low dissipation constant, i.e., $$\frac{R}{k_t^2}$$

less than about 50 W/(Nm)$^2$, can deliver high torque with low winding loss compared to other motors having a greater dissipation constant. As such, the motor 104 dissipates less heat, keeping the prosthesis 100 cool, and also requires less power, thereby increasing battery life.

In operation, in addition to providing torque to the ankle pivot 110 (e.g., at or near the end of the controlled dorsiflexion phase and/or in the powered plantar flexion phase of the gait cycle) the motor 104 may also provide an impedance and joint equilibrium to the ankle pivot 110, for example, to achieve an ankle (joint, in general) equilibrium trajectory during the swing phase of the gait cycle. Similarly, as in the application of torque as described above, the motor 104 can cause displacement of the ball nut 120, applying a force to the series spring 108 which, in turn, provides the required impedance to the ankle pivot 110 with respect to the joint, equilibrium trajectory.

In some embodiments, the motor leads are shorted, such that the motor draws substantially no current and operates as a dynamic mechanical clutch. This can enable an ankle or other augmentation device to provide stability during loss of battery or system malfunction. The shorted leads mode exerts a viscous damping torque on the motor, proportional to $k_t^2/R$. As measured at the output of the transmission, the viscous damping is amplified by the square of the gear ratio, kg, yielding a transmission damping, B, of kg$^2 \times k_t^2/R$. For an SEA with series stiffness, $K_{SEA}$, the time constant of the dynamic (viscous) clutch is $B/K_{SEA}$. In some embodiments that store energy in the series spring for rapid release later, it is useful to apply the viscous clutch at a time when the desired spring energy is achieved. Within a small time period in relation to the time constant above, the transmission is effectively a static brake, enabling the spring to release and deliver power to the joint. Such a mode of operation is useful in slow walking, where consistent and quiet power is desired, and in running, where the ankle functions primarily as a spring, and the series spring release occurs in less than 50 milliseconds. Such a mode is also useful in control of a knee in early stance, to deliver high torque through the series spring with no battery power. In all of the above embodiments, the clutch is used to apply high torque but without substantially drawing energy from the battery.

Thus, in general, in an SEA having a certain gear ratio and a certain series spring constant, the smaller the motor dissipation, constant the longer the duration for which the applied stiffness (a component of the impedance) can be substantially maintained, after shorting the motor leads. Thus, in an SEA using a motor having a large dissipation constant and, consequently, having a duration for which stiffness can be substantially maintained without drawing current that is shorter than the time period for which the equilibrium needs to be maintained, the power supplied to the motor cannot be turned off without adversely affecting the joint (e.g., ankle) equilibrium. In the SEA 102, however, if the gear ratio of the transmission 106 is about 40:1. the motor dissipation constant is about 10, and the spring constant of the series spring 108 is about 400, the SEA 102 can maintain the applied stiffness for a time constant (i.e., holding time) of about 250 milliseconds. Typically during the stance phase of the gait cycle while walking or running, this holding time is sufficient to maintain a roughly fixed joint equilibrium for a required duration, typically about 50-100 milliseconds for walking and running. Accordingly, as the motor 104 draws substantially zero current after shorting the leads, a Anther reduction in the power consumption of the SEA 102 is achieved while simultaneously achieving ankle equilibrium.

With reference to FIG. 1C, the three-phase stator assembly 122 of the motor 104 wraps around the rotor 124 to facilitate mounting of the motor to the prosthesis housing, e.g., using a needle bearing component, A bellows 126 protects the screw 114 from contamination. The ball-nut 120 employs an end-flexure 128 to isolate the thrust bearings 118 from out-of-plane moment loads as shown in Section A-A in FIG. 1B, The end-flexure 128 can move side-to-side so as to eliminate side-loads, further isolating the thrust bearings 118 from moments applied by the series spring 108. Typically, thrust loads on the end-flexure 128 are supported by needle bearings press fit into a end-flexure mounting hole 130.

Figure 2:
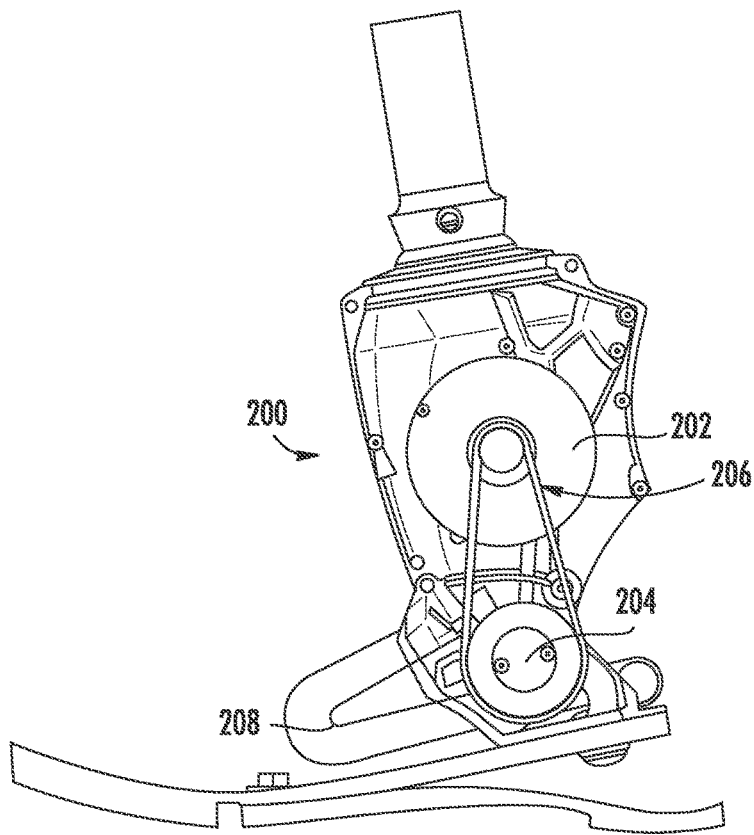
FIG. 2 illustrates a powered actuator employing a cable transmission, according to one embodiment, for use with ankle prostheses.

FIG. 2 depicts a biomimetic ankle-foot prosthesis that uses a direct-drive rotary actuator 200 with a cable transmission. The actuator 200 employs a high-torque, transverse-flux, external rotor motor 202 to directly drive the ankle output pulley 204 via a cable 206. The cable can be a synthetic cable or a steel cable. In some embodiments, a belt or a chain drive may be used instead of a synthetic or steel cable. Motors other than transverse flux motors, but having an external rotor may also be used. A rotary series spring connects the ankle output pulley 204 to the ankle output joint 208. The rotor of the motor 202 may be captivated by ankle shells using needle bearings.

Absolute angular displacement of the ankle output pulley 204 and of the rotor of the motor 202 may be used, as described above with reference to FIGS. 1A and 1B to determine the state of the actuator 200. Magnetic field angle encoders may be used instead of absolute encoders. The flex in the cable 206 may be measured based on the span (length) of the cable, which is related to the difference between the output joint position and the motor position. With high resolution encoders, cable stretch can be sensed with sufficient bandwidth and resolution for closed-loop control. The flex in the cable 206 can then be compensated in an output torque feedback loop. The cable 206 in the actuator 200 can achieve a gear ratio, i.e., the ratio of the motor angle and the angle of the output joint, i.e., ankle pivot 208, of about 20:1, in one embodiment.

Figure 3C:
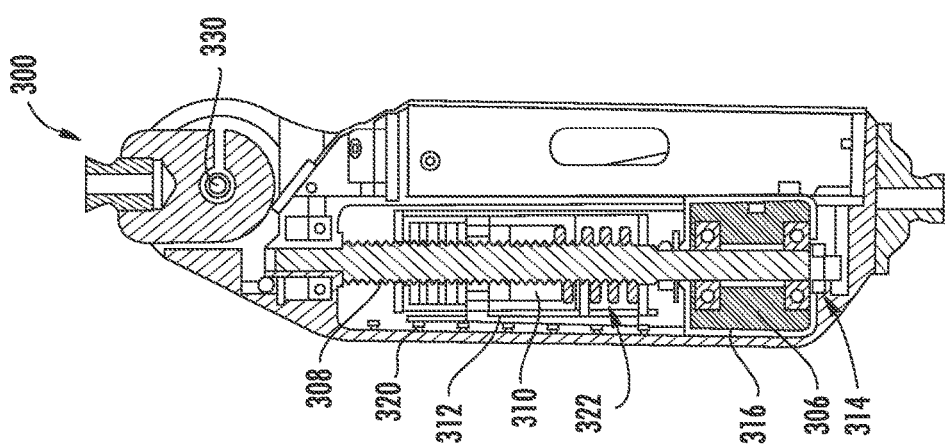
Figure 6:
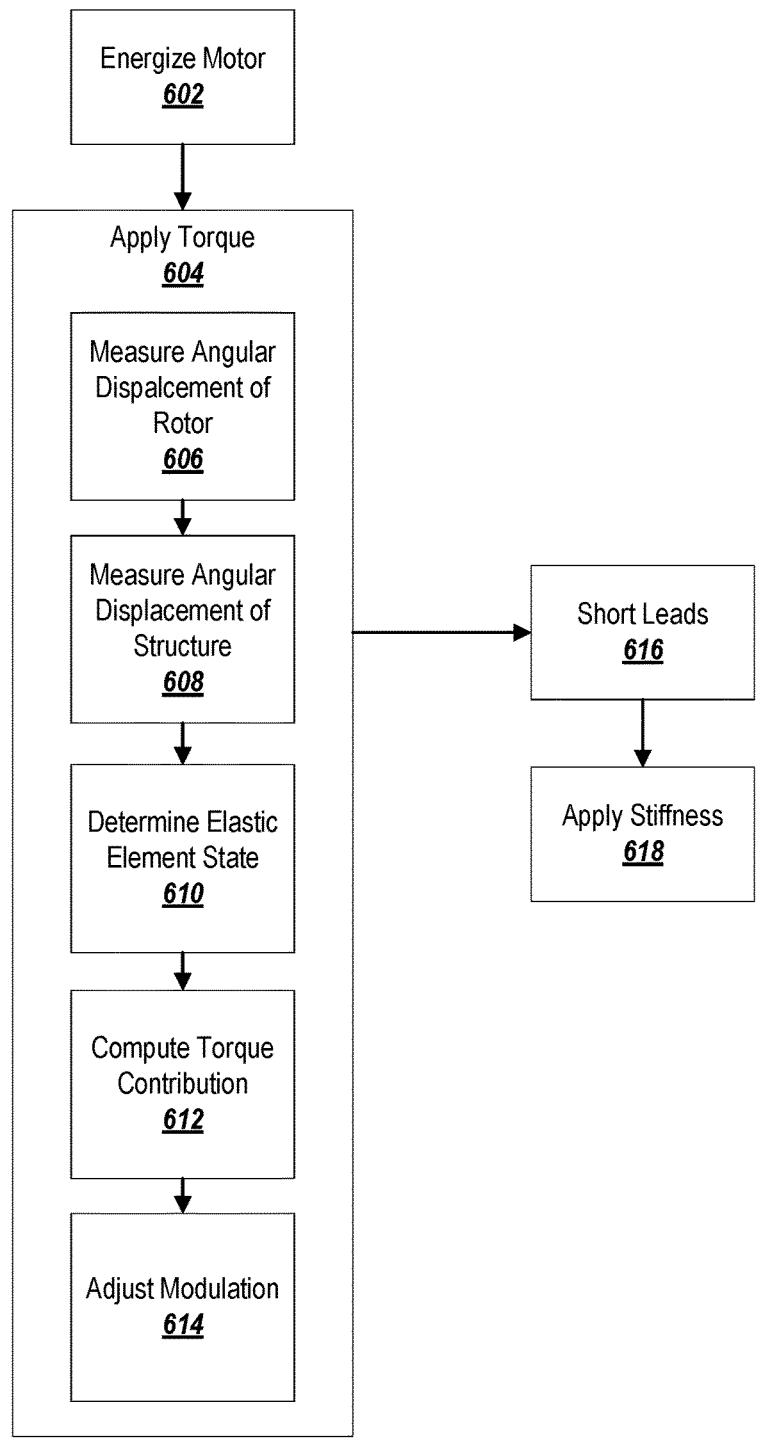
FIG. 6 is a flowchart depicting an exemplary method table of certain, design, and operating parameters of powered, actuators according to various embodiments.

FIGS. 3A-3C illustrate a biomimetic knee prosthesis 300 that uses a direct-drive, ball-screw based system coupled to a series spring connecting the ball-screw transmission to the knee joint output. The device 300 controls the equilibrium position of the knee joint 302, and applies torque or impedance to the knee joint 302 substantially along the centerline of the output pulley 304, The knee prosthesis 300 can deliver about 200 Nm of torque over a range of about 120 degrees of angular displacement of the artificial knee joint 302 useful for stair and steep ramp ascent as well as for level ground walking. A transverse-flux, motor 306 (or other high-torque, external rotor motor) drives a screw 308 thereby driving a ball-nut 310 supported by a linear rail 312. A retaining nut 314 preloads the angular contact bearings 316 inside the motor 306.

A cable attachment device 318, also supported by the linear rail 312, connects to the ball-nut 310 via series springs 320, 322 and linearly drives the cable 324. The cable 324 wraps around a light-weight pulley 326, an idler pulley 328, and the output pulley 304 to apply torque/impedance to the knee joint 302 about the knee axis 230. The cable 324 can be a synthetic cable, a steel cable, a belt, or a chain drive.

The pitch of the ball screw 308 is in the range of approximately 6 mm up to about 10 mm so as to achieve a low gear ratio of less than about 30:1, or less than, about 20:1. The gear ratio is a ratio of the respective angular displacements of the rotor of motor 306 and the knee joint 302. An absolute magnetic encoder 330 having at least a 13-bit resolution (e.g. RMB-20 manufactured by Renishaw), is used to measure the angular displacement of the motor rotor in relation to the stator, and an absolute magnetic encoder 334, which may also have at least a 13-bit resolution, is used to measure the angular displacement of the lower knee structure relative to the upper knee structure. The motor and knee joint angles are used, respectively, to determine the states of the motor 306 and the knee 302, and can also be used to estimate the state of the series springs 320, 322. For redundancy in sensing, a linear series-spring deflection potentiometer 336 is optionally included to measure series-spring deflections directly. Based on the series spring state and stiffness (i.e., spring constant), series-elastic actuator force and joint torque supplied by the SEA can be determined, (See for example, the co-pending U.S. patent application Ser. No. 13/079564 "Controlling Power in a Prosthesis or Orthosis Based on Predicted Walking Speed or Surrogate for Same" filed on Apr. 4, 2011; U.S. patent application Ser. No. 13/079571 "Controlling Torque in. a Prosthesis or Orthosis Based on a Deflection of Series Elastic Element" filed, on Apr. 4, 2011).

Figure 4:
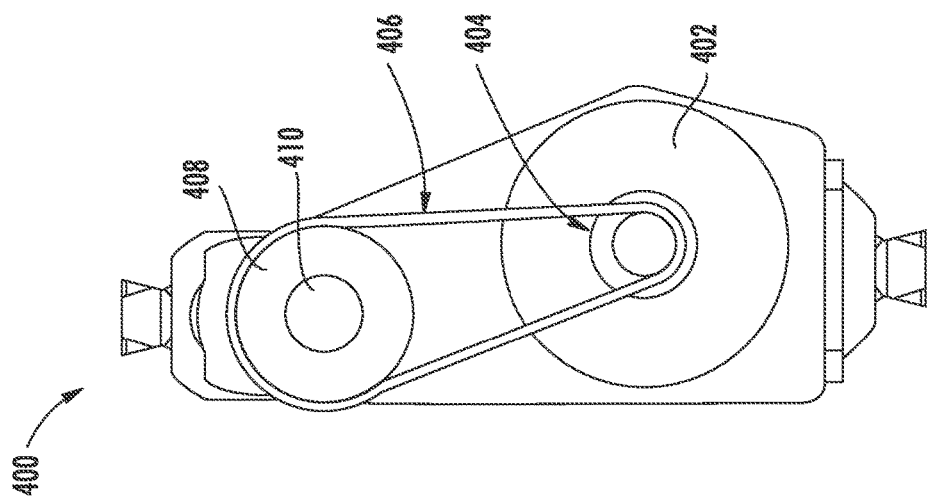
FIG. 4 illustrates a powered actuator employing a cable transmission, according to one embodiment, for use with knee prostheses.

FIG. 4 depicts a biomimetic knee prosthesis that uses a direct-drive rotary actuator 400 using cable transmission, similar to that described above with reference to FIG. 2. A high-torque external rotor motor 402 (e.g., a transverse flux motor) is configured in a "pancake" arrangement to minimize stack height and to maximize torque-current gain. The motor 402 drives a pulley 404 and, through a direct-cable transmission 406, drives the output pulley 408. A rotary series spring couples the knee output pulley 418 to the knee output joint 410. Thus, rotating the output pulley 408, in turn, causes the knee joint 410 to rotate. Absolute encoders on the motor 402 and on the output pulley 408 may be used to measure the state of the actuator 400 similarly as described above with reference to FIGS. 1A and 1B. The SEA 400 yields a low gear ratio, i.e., the ratio of the motor angle and the knee joint angle, of about 20:1.

Although various direct-drive SEAs are described above as components of wearable robot ankle and knee prosthetic devices, this is for illustrative purposes only. Hip prosthetic devices are also contemplated. To those skilled in the art, it should be apparent that these SEAs can be readily adapted for use in wearable robot ankle, knee, and hip orthotic devices, wearable robots for upper-extremity orthotic and prosthetic devices, and in humanoid robots. It should also be understood that although the powered actuators, described herein take advantage of some of the key attributes of transverse flux motors, specifically high torque density and efficiency, these actuators can also leverage other high-torque motors, including hybrid stepping motors, induction motors, traditional radially-applied permanent magnet motors, and variable reluctance motors. The speed of these motors may be less than 5000 rpm, or less than 1500 rpm, or less than 300 rpm, depending on the optimum system design as defined by the motor, transmission gear ratio, series-spring stiffness, parallel elasticity, and battery power source; optimum generally referring to a tradeoff of battery economy per stride, design life of the transmission, and device weight. Table 1 in FIG. 5 shows various design and operating parameters of the powered SEAs according to various embodiments. The minimum, typical, and maximum values of these parameters are also listed in Table 1. A typical wearer weighs in the range from about 190 lbs up to about 250 lbs. Wearer mass is used to normalize the actuator weight. Series Stiffness (i.e., spring constant of the serially connected elastic element) and Parallel Stiffness (i.e., spring constant of the optional elastic element connected in parallel with the serially connected elastic element).

While the invention, has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. A method for augmenting joint function using a powered human augmentation device, the method comprising:

energizing a motor in the human augmentation device to apply torque to a joint of the human augmentation device during a phase of a gait cycle to modulate at least one of joint augmentation torque, joint impedance, or joint equilibrium during the phase of the gait cycle, the applied torque normalized by weight to be between −2.8 Nm/kg to 2.8 Nm/kg, the motor coupled directly to a transmission, the transmission being serially coupled to an elastic element, the elastic element coupled to the joint; and shorting leads of the motor to exert a viscous damping torque on the motor proportional to a motor dissipation constant given by $R/k_1^2$, where R refers to a stator winding resistance and $k_1$ refers to a motor torque constant, the dissipation constant being less than 50 $W/(Nm)^2$.

2. The method of claim 1, the dissipation constant being about 10 $W/(Nm)^2$.

3. The method of claim 1, the transmission comprising a gear ratio, the gear ratio less than 80:1.

4. The method of claim 1, further comprising energizing the motor to apply stiffness to the joint, the elastic element configured to store energy and to release the stored energy as power, the motor applying power to augment the power of the elastic element to achieve a positive torque feedback response.

5. The method of claim 1, comprising:

energizing the motor to apply the torque to achieve a desired joint equilibrium position; and shorting leads of the motor during a stance phase of the gait cycle to substantially maintain the joint equilibrium position during a portion of the stance phase.

6. The method of claim 1, comprising:

measuring angular displacement of a rotor of the motor with respect to a stator of the motor;

measuring angular displacement of a structure with respect to the joint;

determining, using a hardware controller of the powered human augmentation device, a state of the elastic element based, at least in part, on both the angular displacement of the rotor and the angular displacement of the structure;

computing, based at least in part on the state of the elastic element and the angular displacement on the motor, a torque contribution of the motor using the hardware controller; and adjusting the modulating, based at least in part on the computed contribution of the motor torque.

\* \* \* \* \*